US011789008B2

(12) United States Patent
Love et al.

(10) Patent No.: US 11,789,008 B2
(45) Date of Patent: Oct. 17, 2023

(54) SYSTEMS, DEVICES, AND METHODS FOR WIRELESS COMMUNICATIONS IN ANALYTE MONITORING SYSTEMS

(71) Applicant: ABBOTT DIABETES CARE INC., Alameda, CA (US)

(72) Inventors: Michael R. Love, Pleasanton, CA (US); Michael J. Fullmer, Alameda, CA (US); Kurt E. Leno, San Leandro, CA (US); Xuandong Hua, Mountain View, CA (US); Mark Sloan, Redwood City, CA (US); Lei He, Moraga, CA (US); Glenn Berman, Alameda, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 17/967,523

(22) Filed: Oct. 17, 2022

(65) Prior Publication Data
US 2023/0145119 A1 May 11, 2023

Related U.S. Application Data

(63) Continuation of application No. 16/541,572, filed on Aug. 15, 2019, now abandoned, which is a
(Continued)

(51) Int. Cl.
*G01N 33/49* (2006.01)
*A61B 5/00* (2006.01)
(Continued)

(52) U.S. Cl.
CPC ......... *G01N 33/492* (2013.01); *A61B 5/0022* (2013.01); *A61B 5/0026* (2013.01);
(Continued)

(58) Field of Classification Search
CPC .. G01N 33/492; A61B 5/0022; A61B 5/0026; A61B 5/14532; A61B 5/1112;
(Continued)

(56) References Cited

U.S. PATENT DOCUMENTS 6,175,752 B1 1/2001 Say et al.
6,377,894 B1 4/2002 Deweese et al.
(Continued)

FOREIGN PATENT DOCUMENTS

WO WO 2015/065775 A2 5/2015

OTHER PUBLICATIONS

Fawaz, K, et al., "Protecting Privacy of BLE Device Users", 25th USENIX Security Symposium, Austin, Texas, 2016, pp. 1205-1221.
(Continued)

*Primary Examiner* — Kerri L McNally
*Assistant Examiner* — Thang D Tran
(74) *Attorney, Agent, or Firm* — ONE LLP

(57) ABSTRACT

Systems, devices and methods are provided that allow for enhanced performance, power efficiency, interoperability, data security and user privacy for in vivo analyte monitoring systems that utilize wireless communications. The in vivo analyte monitoring systems can include a Bluetooth or Bluetooth Low Energy enabled handheld relay device for wirelessly relaying analyte data between a sensor unit device and one or more reader devices. The in vivo analyte monitoring systems can employ advertisement and encryption schemes for wirelessly transmitting data in a manner that allows for improved security, efficiency and privacy.

15 Claims, 13 Drawing Sheets

Related U.S. Application Data continuation of application No. 15/846,172, filed on Dec. 18, 2017, now abandoned.

(60) Provisional application No. 62/437,014, filed on Dec. 20, 2016.

(51) Int. Cl.
    | | |
    |---|---|
    | *A61B 5/145* | (2006.01) |
    | *H04W 4/80* | (2018.01) |
    | *H04W 4/38* | (2018.01) |
    | *H04W 12/02* | (2009.01) |
    | *A61B 5/11* | (2006.01) |
    | *H04W 12/71* | (2021.01) |

(52) U.S. Cl.
    CPC .......... *A61B 5/14532* (2013.01); *H04W 4/38* (2018.02); *H04W 4/80* (2018.02); *H04W 12/02* (2013.01); *A61B 5/1112* (2013.01); *A61B 5/1451* (2013.01); *A61B 5/14507* (2013.01); *A61B 5/14546* (2013.01); *A61B 5/6802* (2013.01); *A61B 5/6898* (2013.01); *A61B 5/7475* (2013.01); *H04W 12/71* (2021.01); *Y02D 30/70* (2020.08)

(58) Field of Classification Search
    CPC .............. A61B 5/14507; A61B 5/1451; A61B 5/14546; A61B 5/6802; A61B 5/6898; A61B 5/7475; H04W 4/38; H04W 4/80; H04W 12/02; H04W 12/71; Y02D 30/70
    USPC .......................................................... 340/500
    See application file for complete search history.

(56) References Cited

U.S. PATENT DOCUMENTS

| | | | |
|---|---|---|---|
| 6,616,819 | B1 | 9/2003 | Liamos et al. |
| 7,418,285 | B2 | 8/2008 | Ghesquiere et al. |
| 7,749,740 | B2 | 7/2010 | Eiteman et al. |
| 7,811,231 | B2 | 10/2010 | Jin et al. |
| 8,867,245 | B1 | 10/2014 | Hwang |
| 9,723,082 | B2 | 8/2017 | Sloan et al. |
| 9,949,642 | B2 | 4/2018 | Love et al. |
| 2002/0084806 | A1 | 7/2002 | Yang |
| 2003/0232632 | A1 | 12/2003 | Lim |
| 2004/0118704 | A1 | 6/2004 | Wang et al. |
| 2004/0125759 | A1 | 7/2004 | Yochem et al. |
| 2004/0158163 | A1 | 8/2004 | Cohen et al. |
| 2005/0003470 | A1 | 1/2005 | Nelson et al. |
| 2006/0091006 | A1 | 5/2006 | Wang et al. |
| 2007/0144918 | A1 | 6/2007 | Hsu et al. |
| 2008/0039702 | A1 | 2/2008 | Hayter et al. |
| 2008/0060955 | A1 | 3/2008 | Goodnow |
| 2008/0066305 | A1 | 3/2008 | Wang et al. |
| 2008/0089250 | A1* | 4/2008 | Jung .................... H04L 5/14 370/276 |
| 2008/0267823 | A1 | 10/2008 | Wang et al. |
| 2008/0278331 | A1 | 11/2008 | Hayter et al. |
| 2008/0281179 | A1 | 11/2008 | Fennell et al. |
| 2008/0281840 | A1 | 11/2008 | Fennell et al. |
| 2009/0105598 | A1 | 4/2009 | Williams et al. |
| 2009/0143661 | A1 | 6/2009 | Taub et al. |
| 2009/0157358 | A1 | 6/2009 | Kim |
| 2009/0198118 | A1 | 8/2009 | Hayter et al. |
| 2009/0245150 | A1* | 10/2009 | Tsao ................... H04W 60/005 370/311 |
| 2009/0247857 | A1 | 10/2009 | Harper et al. |
| 2010/0094110 | A1 | 4/2010 | Heller et al. |
| 2010/0094111 | A1 | 4/2010 | Heller et al. |
| 2010/0094112 | A1 | 4/2010 | Heller et al. |
| 2010/0288632 | A1 | 11/2010 | Say et al. |
| 2010/0324392 | A1 | 12/2010 | Yee et al. |
| 2010/0331646 | A1 | 12/2010 | Hoss et al. |
| 2011/0054282 | A1 | 3/2011 | Nekoomaram et al. |
| 2011/0060530 | A1 | 3/2011 | Fennell |
| 2011/0082484 | A1 | 4/2011 | Saravia et al. |
| 2011/0106126 | A1 | 5/2011 | Love et al. |
| 2011/0184264 | A1 | 7/2011 | Galasso et al. |
| 2011/0190603 | A1 | 8/2011 | Stafford |
| 2011/0191044 | A1 | 8/2011 | Stafford |
| 2011/0193704 | A1 | 8/2011 | Harper et al. |
| 2011/0213225 | A1* | 9/2011 | Bernstein ............... G16H 40/67 600/309 |
| 2011/0288574 | A1 | 11/2011 | Curry et al. |
| 2011/0315564 | A1 | 12/2011 | Guthrie et al. |
| 2011/0319729 | A1 | 12/2011 | Donnay et al. |
| 2012/0088995 | A1 | 4/2012 | Fennell et al. |
| 2012/0197222 | A1 | 8/2012 | Donnay et al. |
| 2012/0245447 | A1 | 9/2012 | Karan et al. |
| 2012/0262716 | A1 | 10/2012 | Wang et al. |
| 2013/0116524 | A1 | 5/2013 | Cole et al. |
| 2013/0127627 | A1 | 5/2013 | Hayter et al. |
| 2013/0150691 | A1 | 6/2013 | Pace et al. |
| 2013/0163126 | A1 | 6/2013 | Dong |
| 2013/0184547 | A1 | 7/2013 | Taub et al. |
| 2013/0274581 | A1 | 10/2013 | Choi et al. |
| 2014/0118104 | A1 | 5/2014 | Sicurello et al. |
| 2014/0121488 | A1 | 5/2014 | Budiman |
| 2014/0172309 | A1 | 6/2014 | Guthrie |
| 2014/0176338 | A1* | 6/2014 | He ........................ H04Q 9/00 340/870.02 |
| 2014/0238874 | A1 | 8/2014 | Elder et al. |
| 2014/0275898 | A1 | 9/2014 | Taub et al. |
| 2014/0299483 | A1 | 10/2014 | Lloyd et al. |
| 2014/0318986 | A1 | 10/2014 | Elder et al. |
| 2014/0318987 | A1 | 10/2014 | Guthrie et al. |
| 2014/0370943 | A1 | 12/2014 | Suhonen |
| 2015/0011970 | A1* | 1/2015 | Kamen .................. G16H 10/65 604/151 |
| 2015/0018643 | A1* | 1/2015 | Cole .................... A61B 5/0015 600/316 |
| 2015/0083609 | A1 | 3/2015 | Elder et al. |
| 2015/0123641 | A1 | 5/2015 | Dalton et al. |
| 2015/0177174 | A1 | 6/2015 | Elder et al. |
| 2015/0177176 | A1 | 6/2015 | Massari et al. |
| 2015/0177256 | A1 | 6/2015 | Elder et al. |
| 2015/0182115 | A1 | 7/2015 | DeHennis |
| 2015/0205947 | A1* | 7/2015 | Berman ................. G16H 40/67 726/16 |
| 2015/0207796 | A1* | 7/2015 | Love ...................... H04L 63/10 726/4 |
| 2015/0245369 | A1* | 8/2015 | Heydon ................ H04W 12/50 370/329 |
| 2015/0330937 | A1* | 11/2015 | Guthrie .............. G01N 27/3273 205/792 |
| 2016/0014550 | A1* | 1/2016 | Chiddarwar ............ H04W 4/80 455/41.2 |
| 2016/0022225 | A1 | 1/2016 | Palmer et al. |
| 2016/0151012 | A1 | 6/2016 | Bozkurt et al. |
| 2016/0227351 | A1* | 8/2016 | Gu ....................... H04B 17/318 |
| 2016/0255704 | A1* | 9/2016 | Mueller ................. H05B 47/19 315/307 |
| 2016/0345874 | A1* | 12/2016 | Raisoni ................ A61B 5/0022 |
| 2017/0013547 | A1* | 1/2017 | Skaaksrud ........... H04W 24/08 |
| 2017/0094446 | A1 | 3/2017 | Maggiore |
| 2017/0339100 | A1* | 11/2017 | Lee ........................ H04W 4/80 |
| 2017/0351828 | A1 | 12/2017 | Cronin et al. |
| 2018/0049199 | A1 | 2/2018 | Skillermark et al. |
| 2018/0103030 | A1 | 4/2018 | Einberg et al. |
| 2018/0145641 | A1 | 5/2018 | Schleicher |
| 2018/0152917 | A1 | 5/2018 | Knaappila et al. |

OTHER PUBLICATIONS

Specification of the Bluetooth System, vol. 0—Master Table of Contents & Compliance Requirements, Covered Core Package version: 4.0, Jun. 30, 2010.

Specification of the Bluetooth System, vol. 1—Architecture & Terminology Overview, Covered Core Package version: 4.0, Jun. 30, 2010.

(56) References Cited

OTHER PUBLICATIONS

Specification of the Bluetooth System, vol. 2—Core System Package [BR/EDR Controller volume], Covered Core Package version: 4.0, Jun. 30, 2010.
Specification of the Bluetooth System, vol. 3—Core System Package [Host volume], Covered Core Package version: 4.0, Jun. 30, 2010.
Specification of the Bluetooth System, vol. 4—Host Controller Interface [Transport Layer], Covered Core Package version: 4.0, Jun. 30, 2010.
Specification of the Bluetooth System, vol. 5—Core System Package [AMP Controller volume], Covered Core Package version: 4.0, Jun. 30, 2010.
Specification of the Bluetooth System, vol. 6—Core System Package [Low Energy Controller volume], Covered Core Package version: 4.0, Jun. 30, 2010.
Specification of the Bluetooth System, vol. 0—Master Table of Contents & Compliance Requirements, Covered Core Package version: 4.2, Dec. 2, 2014.
Specification of the Bluetooth System, vol. 1—Architecture & Terminology Overview, Covered Core Package version: 4.2, Dec. 2, 2014.
Specification of the Bluetooth System, vol. 2—Core System Package [BR/EDR Controller volume], Covered Core Package version: 4.2, Dec. 2, 2014.
Specification of the Bluetooth System, vol. 3—Core System Package [Host volume], Covered Core Package version: 4.2, Dec. 2, 2014.
Specification of the Bluetooth System, vol. 4—Host Controller Interface [Transport Layer], Covered Core Package version: 4.2, Dec. 2, 2014.
Specification of the Bluetooth System, vol. 5—Core System Package [AMP Controller volume], Covered Core Package version: 4.2, Dec. 2, 2014.
Specification of the Bluetooth System, vol. 6—Core System Package [Low Energy Controller volume], Covered Core Package version: 4.2, Dec. 2, 2014.
Specification of the Bluetooth System, vol. 7—Core System Package [Wireless Coexistence volume], Covered Core Package version: 4.2, Dec. 2, 2014.
Wooley, M., "Bluetooth Technology Protecting Your Privacy", retrieved from http://blog.bluetooth.com/bluetooth-technology-protecting-your-privacy, 2015, pp. 1-5.
WO, PCT/US2017/067145 Invitation to Pay Additional Fees, dated Apr. 6, 2018.
WO, PCT/US2017/067145 ISR and Written Opinion, dated Jun. 5, 2018.

* cited by examiner

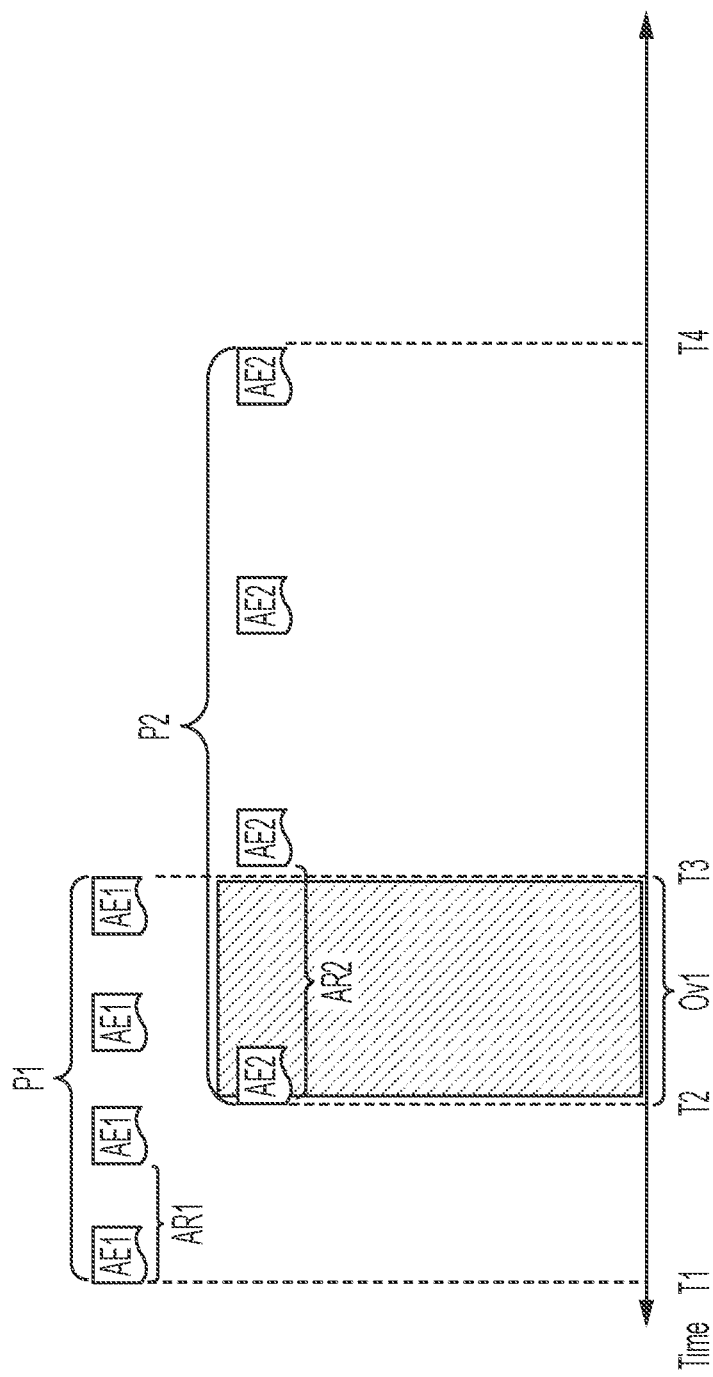

SYSTEMS, DEVICES, AND METHODS FOR WIRELESS COMMUNICATIONS IN ANALYTE MONITORING SYSTEMS

CROSS-REFERENCE TO RELATED APPLICATIONS

The present application is a continuation of U.S. patent application Ser. No. 16/541,572, filed Aug. 15, 2019, which is a continuation of U.S. patent application Ser. No. 15/846,172, filed Dec. 18, 2017, now abandoned, which claims priority to and the benefit of U.S. Provisional Patent Application No. 62/437,014, filed Dec. 20, 2016, all of which are incorporated by reference herein in its entirety for all purposes.

FIELD

The subject matter described herein relates to systems, devices, and methods for wireless communications in analyte monitoring devices.

BACKGROUND

The detection and/or monitoring of analyte levels, such as glucose, ketones, lactate, oxygen, hemoglobin A1C, or the like, can be vitally important to the health of an individual having diabetes. Patients suffering from diabetes mellitus can experience complications including loss of consciousness, cardiovascular disease, retinopathy, neuropathy, and nephropathy. Diabetics are generally required to monitor their glucose levels to ensure that they are being maintained within a clinically safe range, and may also use this information to determine if and/or when insulin is needed to reduce glucose levels in their bodies or when additional glucose is needed to raise the level of glucose in their bodies.

Growing clinical data demonstrates a strong correlation between the frequency of glucose monitoring and glycemic control. Despite such correlation, many individuals diagnosed with a diabetic condition do not monitor their glucose levels as frequently as they should due to a combination of factors including convenience, testing discretion, pain associated with glucose testing, and cost.

As described in further detail below, one type of monitoring system is an in vivo analyte monitoring system, in which a sensor control device may be worn on the body of an individual that requires analyte monitoring. The sensor control device may have a small form-factor to increase comfort and convenience for the individual. The sensor control device may also be configured to wirelessly transmit analyte data to another device, on which the individual or her health care provider (HCP) can review the individual's data and make therapy decisions. Due to certain aspects of wireless communication protocols and the compact size of the sensor control device in these in vivo analyte monitoring systems, problems may arise relating to power management, signal noise interference, interoperability, data security and privacy.

For these and other reasons, needs exist for improved analyte monitoring systems, devices, and methods.

SUMMARY

The use of wireless communication protocols within an in vivo analyte monitoring system may present problems relating to power management, signal noise interference, interoperability, data security and privacy, to name a few. These problems can arise because manufacturers of sensor control devices may have little control over a user's reader devices (e.g., smartphones) and their associated operating systems. For example, a reader device's operating system may require that a sensor control device turn its communication circuitry (e.g., its transceiver) on and off at a frequent rate, which can create signal noise interference and rapid power consumption in the sensor control device. In addition, third party user interface applications on the reader device may prevent important information from being conveyed to and/or received by the user.

Furthermore, in recent years, the threat of unauthorized tracking of wireless devices has become a greater concern. For example, third parties may surreptitiously operate wireless device "trackers" at various geographical locations, which are designed to track the movement of an individual through a particular region based on an address of the wireless device. Thus, manufacturers have a need for enhanced privacy countermeasures, in particular, because in many embodiments, sensor control devices are designed to be continuously worn on the body of the user.

A number of embodiments of systems, devices and methods are provided that allow for improved power management, operation, interoperability, security and privacy for in vivo analyte monitoring systems utilizing wireless communication protocols. For example, in certain embodiments, a handheld relay device can be used to relay data indicative of a sensed analyte level between a sensor control device and one or more reader devices. In some embodiments, power latch circuitry can be used to activate devices having a test strip interface. As described herein, these embodiments and others can allow for reduced power consumption by sensor control devices and improved interoperability with a diverse range and number of reader devices and their respective operating systems. In further embodiments, advertising schemes for wireless protocols are described which can allow for increased security through encrypted analyte data carried in advertisement communications and enhanced privacy through anti-tracking routines.

Other systems, devices, methods, features and advantages of the subject matter described herein will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 5A is a timeline diagram depicting an example embodiment of an advertising scheme for use with an in vivo analyte monitoring system.

DETAILED DESCRIPTION

Figure 1A:
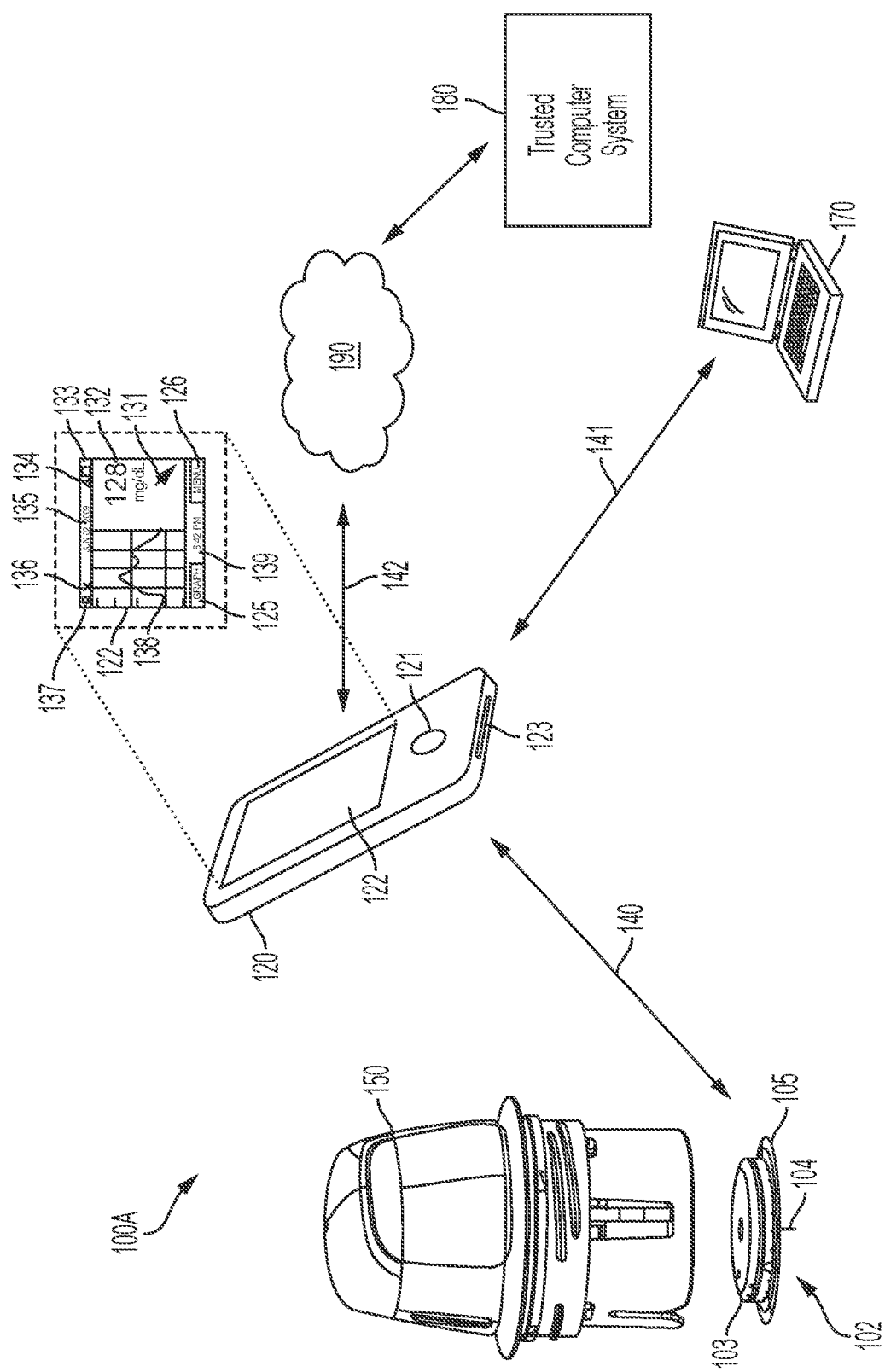
FIG. 1A is a high level diagram depicting an example embodiment of an in vivo analyte monitoring system.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

As used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

Generally, embodiments of the present disclosure are used with systems, devices, and methods for detecting at least one analyte, such as glucose, in a bodily fluid (e.g., subcutaneously within the interstitial fluid ("ISF") or blood, within the dermal fluid of the dermal layer, or otherwise). Accordingly, many embodiments include in vivo analyte sensors structurally configured so that at least a portion of the sensor is, or can be, positioned in the body of a user to obtain information about at least one analyte of the body. It should be noted, however, that the embodiments disclosed herein can be used with in vivo analyte monitoring systems that incorporate in vitro capability, as well as purely in vitro or ex vivo analyte monitoring systems, including those systems that are entirely non-invasive.

Furthermore, for each and every embodiment of a method disclosed herein, systems and devices capable of performing each of those embodiments are covered within the scope of the present disclosure. For example, embodiments of sensor control devices are disclosed and these devices can have one or more sensors, analyte monitoring circuits (e.g., an analog circuit), memories (e.g., for storing instructions), power sources, communication circuits, transmitters, receivers, processors and/or controllers (e.g., for executing instructions) that can perform any and all method steps or facilitate the execution of any and all method steps. These sensor control device embodiments can be used and can be capable of use to implement those steps performed by a sensor control device from any and all of the methods described herein.

Likewise, embodiments of handheld relay devices and reader devices are disclosed having one or more transmitters, receivers, memories (e.g., for storing instructions), power sources, processors and/or controllers (e.g., for executing instructions) that can perform any and all method steps or facilitate the execution of any and all method steps. These embodiments of the handheld relay devices and reader devices can be used to implement those steps performed by a handheld relay device or reader device from any and all of the methods described herein.

Embodiments of trusted computer systems are also disclosed. These trusted computer systems can include one or more processors, controllers, transmitters, receivers, memories, databases, servers, and/or networks, and can be discretely located or distributed across multiple geographic locales. These embodiments of the trusted computer systems can be used to implement those steps performed by a trusted computer system from any and all of the methods described herein.

As mentioned, a number of embodiments of systems, devices, and methods are described herein that provide for improved power management, interoperability, data security and privacy for in vivo analyte monitoring systems which utilize wireless communications. These embodiments further allow for signal noise reduction and reduced power consumption by the sensor control device; centralized management of wireless connections between multiple and disparate reader devices through the use of a handheld relay device; enhanced security and privacy measures for wireless communications; to name a few features. Before describing these aspects of the embodiments in detail, however, it is first desirable to describe examples of devices that can be present within, for example, an in vivo analyte monitoring system, as well as examples of their operation, all of which can be used with the embodiments described herein.

There are various types of in vivo analyte monitoring systems. "Continuous Analyte Monitoring" systems (or "Continuous Glucose Monitoring" systems), for example, can transmit data from a sensor control device to a reader device continuously without prompting, e.g., automatically according to a schedule. "Flash Analyte Monitoring" systems (or "Flash Glucose Monitoring" systems or simply "Flash" systems), as another example, can transfer data from a sensor control device in response to a scan or request for data by a reader device, such as with a Near Field Communication (NFC) or Radio Frequency Identification (RFID) protocol. In vivo analyte monitoring systems can also operate without the need for finger stick calibration.

In vivo analyte monitoring systems can be differentiated from "in vitro" systems that contact a biological sample outside of the body (or rather "ex vivo") and that typically include a meter device that has a port for receiving an analyte test strip carrying a bodily fluid of the user, which can be analyzed to determine the user's blood sugar level.

In vivo monitoring systems can include a sensor that, while positioned in vivo, makes contact with the bodily fluid of the user and senses the analyte levels contained therein. The sensor can be part of a sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few.

In vivo monitoring systems can also include one or more reader devices that receive sensed analyte data from the sensor control device either directly or through a handheld relay device, as described in further detail below. These reader devices can process and/or display the sensed analyte data, in any number of forms, to the user. These devices, and variations thereof, can be referred to as "handheld reader devices," "reader devices" (or simply, "readers"), "handheld electronics" (or handhelds), "portable data processing" devices or units, "data receivers," "receiver" devices or units (or simply receivers), or "remote" devices or units, to name a few. Other devices such as personal computers have also been utilized with or incorporated into in vivo and in vitro monitoring systems.

As further described herein, in vivo monitoring systems can also include a handheld relay device that relays sensed analyte data from the sensor control device to a reader device. In a general sense, the handheld relay device can include many of the same functionalities as the reader device. However, the handheld relay device may also include fewer features, such as a non-graphical user interface. In addition, because the handheld relay device and the sensor control device are often provided by the same manufacturer, the handheld relay device may also include additional features not present on reader devices. For example, the handheld relay device may be configured to communicate directly with a sensor control device using a proprietary wireless protocol, and further, can be configured to serve as a central hub from which sensed analyte data can be transmitted to one or more reader devices. Similarly, the handheld relay device can be configured to monitor itself for failure conditions according to parameters that are more rigorous or stringent than reader devices.

For reasons described with more detail below, the use of standard wireless communication protocols within an in vivo analyte monitoring system can pose challenges relating to power management, signal noise interference, interoperability, data security and privacy, to name a few. For wireless communications between a sensor control device and a reader device (e.g., a smartphone), for example, the reader device's operating system may require that the sensor control device turn its communication circuitry (e.g., its transceiver) on and off at a relatively frequent rate. This can create undesirable effects within the in vivo analyte monitoring system such as signal noise interference with sensitive analog sensor readings and rapid power consumption in the sensor control device.

As another example, the periodic release of new and updated operating system software on reader devices may present interoperability challenges in that a sensor control device may not be easily upgraded. Likewise, manufacturers of sensor control devices may have little control over reader devices, particularly where the reader device is a smartphone. In this regard, use of a reader device as a primary display device within an in vivo analyte monitoring system can be problematic in that manufacturers cannot control third party user interface applications installed on the reader device, which may obscure or impair important data, alerts and/or alarms. Thus, a need exists to ensure that sensor control devices and/or reader devices can be operated in a manner that is power efficient, does not interfere with sensor readings, and does not prevent important information from reaching the user.

Furthermore, in recent years, threats relating to the security and privacy of sensitive data communicated within a wireless in vivo analyte monitoring system, such as, for example, "man-in-the-middle" attacks and/or unauthorized tracking of wireless devices, have become a greater concern. As one example, third parties may intercept sensitive patient health information contained within wireless communications between a sensor control device and a reader device during a data transmission procedure. As another example, third parties may surreptitiously operate wireless device "trackers" at various geographical locations, which are designed to track the movement of an individual through a particular region based on an address of the wireless device. While certain wireless communication protocols have included countermeasures against such "trackers," e.g., through the use of random and/or resolvable addresses in Bluetooth and Bluetooth Low Energy devices, these countermeasures have been shown to be inadequate. For instance, third-party trackers can be programmed to associate two or more randomly generated addresses with a particular wireless device. Based on a sequence of observable events in which a first device address disappears, followed by the appearance of a second device address, a tracker may deduce that the two device addresses correlate with a single wireless device.

The aforementioned problems, as well as others described below, are particularly amplified with regards to wireless communications in vivo analyte monitoring systems, since sensor control devices usually have a limited power supply and are designed to be continuously worn on the body of the user. The claimed solutions disclosed herein do not simply transplant a pre-existing practice or problem-solving method into a computer-based environment. Rather, these embodiments specifically address issues of power efficiency, interoperability, privacy and security that exist solely due to the environment of wireless communications within in vivo analyte monitoring systems. By way of a non-limiting example, some embodiments described herein utilize a handheld relay device between the sensor control unit and a reader device (e.g., smart phone). In these embodiments, the handheld relay device can be configured to communicate with the sensor control device using a proprietary wireless protocol, relay data with one or more reader devices, and/or install software updates relating to the various mobile operating systems of the one or more reader devices. In these example embodiments, the sensor control device can operate with reduced signal noise interference, greater power efficiency and fewer interoperability issues. In other example embodiments, to reduce the chance of "main-in-the-middle" attacks, the sensor control device can be configured to enter a state in which it exclusively accepts data and connection requests from the handheld relay device, and moreover, controls the timing interval of communications therewith. In still other example embodiments, to enhance privacy and data transmission efficiency, the sensor control device can utilize advertising schemes wherein multiple and overlapping device addresses are utilized and/or encrypted data can be placed within advertising packets. These example embodiments, as well as others described below, are necessarily rooted in the computer-based technology of wireless communications within in vivo analyte monitoring systems.

Furthermore, for all of the same reasons stated above, these solutions are directed to specific improvements in wireless communications within in vivo analyte monitoring systems, which indisputably constitute a computer-related technology. As one specific example, the use of a proprietary wireless protocol between the sensor control device and a handheld relay device enables the sensor control device to turn on and off the radio transmitter less frequently, resulting in greater power efficiency, less noise, and ultimately, improved sensor performance. Similarly, the use of a handheld relay device to interoperate with multiple reader devices allows for less consumption of power and resources on the sensor control device, and ultimately improved performance. Likewise, the use of a wireless communication advertising scheme with multiple and overlapping device addresses reflects a specific improvement in the privacy and security of data wirelessly transmitted by the sensor control device. Indeed, the elements of each embodiment described herein, when viewed both individually and as an ordered combination, amount to a significant and specific advancement in the technology of wireless communications, and in particular, the power efficiency, interoperability, security and privacy of patient data within in vivo analyte monitoring systems. For these reasons, as well as others, these embodiments are not abstract.

Example Embodiments of In Vivo Analyte Monitoring Systems

FIG. 1A is an illustrative view depicting an example of an in vivo analyte monitoring system 100A having a sensor control device 102 and a reader device 120 that communicate with each other over a local communication path (or link) 140, which can be wired or wireless, and uni-directional or bi-directional. In embodiments where path 140 is wireless, a near field communication (NFC) protocol, RFID protocol, Bluetooth or Bluetooth Low Energy protocol, Wi-Fi protocol, proprietary protocol, or the like can be used, including those communication protocols in existence as of the date of this filing or their later developed variants.

Bluetooth is a well-known standardized short range wireless communication protocol, and Bluetooth Low Energy is a version of the same that requires less power to operate. Bluetooth Low Energy (Bluetooth LE, BTLE, BLE) is also referred to as Bluetooth Smart or Bluetooth Smart Ready. BTLE is described in the Bluetooth Specification, version 4.0, published Jun. 30, 2010, and version 4.2, published Dec. 2, 2014, both of which are explicitly incorporated by reference herein for all purposes. The term "NFC" applies to a number of protocols (or standards) that set forth operating parameters, modulation schemes, coding, transfer speeds, frame format, and command definitions for NFC devices. The following is a non-exhaustive list of examples of these protocols, each of which (along with all of its sub-parts) is incorporated by reference herein in its entirety for all purposes: ECMA-340, ECMA-352, ISO/IEC 14443, ISO/IEC 15693, ISO/IEC 18000-3, ISO/IEC 18092, and ISO/IEC 21481.

Reader device 120 is also capable of wired, wireless, or combined communication with a remote computer system 170 over communication path (or link) 141 and with trusted computer system 180 through network 190 and over communication path (or link) 142. Communication paths 141 and 142 can be part of a telecommunications network, such as a Wi-Fi network, a local area network (LAN), a wide area network (WAN), the internet, or other data network for uni-directional or bi-directional communication. Trusted computer system 180 can be accessed through network 190. In an alternative embodiment, communication paths 141 and 142 can be the same path. All communications over paths 140, 141, and 142 can be encrypted and sensor control device 102, reader device 120, remote computer system 170, and trusted computer system 180 can each be configured to encrypt and decrypt those communications sent and received.

Variants of devices 102 and 120, as well as other components of an in vivo-based analyte monitoring system that are suitable for use with the system, device, and method embodiments set forth herein, are described in US Patent Application Publ. No. 2011/0213225 (the '225 Publication), which is incorporated by reference herein in its entirety for all purposes.

Sensor control device 102 can include a housing 103 containing in vivo analyte monitoring circuitry and a power source. The in vivo analyte monitoring circuitry is electrically coupled with an analyte sensor 104 that extends through an adhesive patch 105 and projects away from housing 103. Adhesive patch 105 contains an adhesive layer (not shown) for attachment to a skin surface of the body of the user. Other forms of body attachment to the body may be used, in addition to or instead of adhesive.

Sensor 104 is adapted to be at least partially inserted into the body of the user, where it can make fluid contact with that user's bodily fluid (e.g., ISF, dermal fluid, or blood) and be used, along with the in vivo analyte monitoring circuitry, to measure analyte-related data of the user. Sensor 104 and any accompanying sensor control electronics can be applied to the body in any desired manner. For example, also shown in FIG. 1A is an embodiment of insertion device 150 that, when operated, transcutaneously (or subcutaneously) positions a portion of analyte sensor 104 through the user's skin and into contact with the bodily fluid, and positions sensor control device 102 with adhesive patch 105 onto the skin. In other embodiments, insertion device 150 can position sensor 104 first, and then accompanying sensor control electronics can be coupled with sensor 104 afterwards, either manually or with the aid of a mechanical device. Other devices, systems, and methods that may be used with embodiments herein, including variations of sensor control device 102, are described, e.g., in U.S. Patent Publication Nos. 2010/0324392, 2011/0106126, 2011/0190603, 2011/0191044, 2011/0082484, 2011/0319729, and 2012/0197222, the disclosures of each of which are incorporated herein by reference for all purposes.

After collecting the analyte-related data, sensor control device 102 can then wirelessly communicate that data (such as, for example, data corresponding to monitored analyte level and/or monitored temperature data, and/or stored historical analyte related data) to a reader device 120 where, in certain embodiments, it can be algorithmically processed into data representative of the analyte level of the user and then displayed to the user and/or otherwise incorporated into a diabetes monitoring regime.

As shown in FIG. 1A, reader device 120 includes a display 122 to output information to the user and/or to accept an input from the user (e.g., if configured as a touch screen), and one optional input component 121 (or more), such as a button, actuator, touch sensitive switch, capacitive switch, pressure sensitive switch, jog wheel or the like, to input data, commands, or otherwise control the operation of reader device 120.

In certain embodiments, input component 121 of reader device 120 may include a microphone and reader device 120 may include software configured to analyze audio input received from the microphone, such that functions and operation of the reader device 120 may be controlled by voice commands. Voice commands can include commands to input data, power cycle a device, retrieve data from sensor control device 102, display data and/or reports, and perform other like operations. In certain embodiments, an output component of reader device 120 includes a speaker (not shown) for outputting information as audible signals. Similar voice responsive components such as a speaker, microphone and software routines to generate, process and store voice driven signals may be provided to sensor control device 102.

In certain embodiments, display 122 and input component 121 may be integrated into a single component, for example, where the display can detect the presence and location of a physical contact touch upon the display, such as a touch screen user interface. In such embodiments, the user may control the operation of reader device 120 by utilizing a set of preprogrammed motion commands, including, but not limited to, single or double tapping the display, dragging a finger or instrument across the display, motioning multiple fingers or instruments toward one another, motioning multiple fingers or instruments away from one another, or other gestures. In certain embodiments, a display includes a touch screen having areas of pixels with single or dual function capacitive elements that serve as LCD elements and touch sensors.

Reader device 120 also includes one or more data communication ports 123 for wired data communication with external devices such as a remote terminal, e.g., a personal computer. Example data communication ports include USB ports, mini USB ports, USB Type-C ports, USB micro-A and/or micro-B ports, RS-232 ports, Ethernet ports, Firewire ports, or other similar data communication ports configured to connect to the compatible data cables. Reader device 120 may also include an integrated or attachable in vitro glucose meter, including an in vitro test strip port (not shown) to receive an in vitro glucose test strip for performing in vitro blood glucose measurements.

Referring still to FIG. 1A, display 122 can be configured to display a variety of information—some or all of which may be displayed at the same or at different times on display 122. The displayed information can be user-selectable so that a user can customize the information shown on a given display screen. Display 122 may include, but is not limited to, graphical display 138, for example, providing a graphical output of current analyte values in real time or over a monitored time period, which may show: markers such as meals, exercise, sleep, heart rate, blood pressure, etc.; numerical display 132, for example, providing monitored glucose values (acquired or received in response to the request for the information); and trend or directional arrow display 131 that indicates a rate of analyte change and/or a rate of the rate of analyte change, e.g., by moving locations on display 122.

As further shown in FIG. 1A, display 122 may also include: date display 135, which can provide date information for the user; time of day information display 139 providing time of day information to the user; battery level indicator display 133 graphically showing the condition of the battery (rechargeable or disposable) of reader device 120; sensor calibration status icon display 134, for example, in monitoring systems that require periodic, routine or a predetermined number of user calibration events notifying the user that the analyte sensor calibration is necessary; audio/vibratory settings icon display 136 for displaying the status of the audio/vibratory output or alarm state; and wireless connectivity status icon display 137 that provides indication of wireless communication connection with other devices such as sensor control device 102, remote computer system 170, and/or trusted computer system 180. Display 122 may further include simulated touch screen buttons 125, 126 for accessing menus, changing display graph output configurations or otherwise controlling the operation of reader device 120.

In certain embodiments, reader device 120 can be configured to output alarms, alert notifications, glucose values, etc., which may be visual, audible, tactile, or any combination thereof. Reader device 120 may include other output components such as a speaker, vibratory output component and the like to provide audible and/or vibratory output indications to the user in addition to the visual output indication provided on display 122. For example, an output unit or display 122 of reader device 120 may be configured to progressively increase or decrease an associated auditory or vibratory signal over a predetermined time period. The output unit of display 122 of the reader device may be further configured to output one or more of a visual, auditory or vibratory signal associated with a connection status associated with another device (e.g., sensor control device 102 or handheld relay device 200). Further details and other display embodiments can be found in, e.g., U.S. Patent Publication No. 2011/0193704, which is incorporated herein by reference for all purposes.

Reader device 120 can be connected to a remote terminal 170, such as a personal computer, which can be used by the user or a medical professional to display and/or analyze the collected analyte data. Reader device 120 can also be connected to a trusted computer system 180 that can be used for authentication of a third party software application. In both instances, reader device 120 can function as a data conduit to transfer the stored analyte level information from the sensor control device 102 to remote terminal 170 or trusted computer system 180. In certain embodiments, the received data from the sensor control device 102 may be stored (permanently or temporarily) in one or more memories of reader device 120.

Remote terminal 170 may be a personal computer, a server terminal, a laptop computer, a tablet, or other suitable data processing device. Remote terminal 170 can be (or include) software for data management and analysis and communication with the components in analyte monitoring system 100. Operation and use of remote terminal 170 is further described in the '225 Publication incorporated herein.

Analyte monitoring system 100 can also be configured to operate with a data processing module (not shown), also as described in the incorporated '225 Publication.

Trusted computer system 180 can be within the possession of the manufacturer or distributor of sensor control device 102, either physically or virtually through a secured connection, and can be used to perform authentication of sensor control device 102. Trusted computer system 180 can also be used for the storage of encryption keys, e.g., identity resolution keys, which are further described below.

Referring now in further detail to reader device 120, that device 120 can be a mobile communication device such as a mobile telephone including, but not limited to, a Wi-Fi or internet enabled smart phone, tablet, or personal digital assistant (PDA). Examples of smart phones can include those mobile phones based on a Windows® operating system, Android™ operating system, iPhone® operating system, Palm® WebOS™, Blackberry® operating system, or Symbian® operating system, with data network connectivity functionality for data communication over an internet connection and/or a local area network (LAN).

Reader device 120 can also be configured as a mobile smart wearable electronics assembly, such as an optical assembly that is worn over or adjacent to the user's eye (e.g., a smart glass or smart glasses, such as Google glasses, which is a mobile communication device). This optical assembly can have a transparent display that displays information about the user's analyte level (as described herein) to the user while at the same time allowing the user to see through the display such that the user's overall vision is minimally obstructed. The optical assembly may be capable of wireless communications similar to a smart phone. Other examples of wearable electronics include devices that are worn around or in the proximity of the user's wrist (e.g., a watch, etc.), neck (e.g., a necklace, etc.), head (e.g., a headband, hat, etc.), chest, or the like.

Figure 1B:
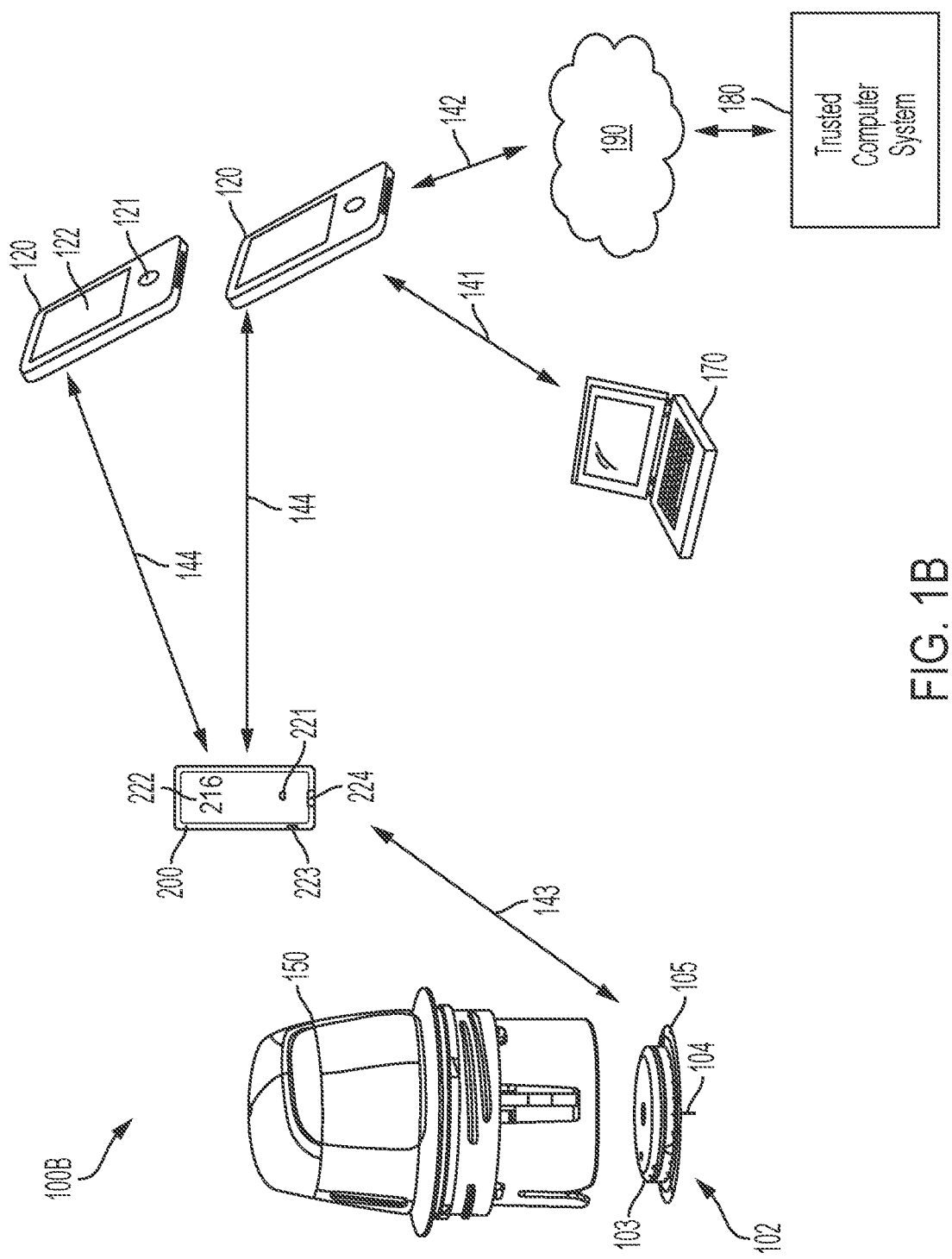
FIG. 1B is a high level diagram depicting another example embodiment of an in vivo analyte monitoring system in which a handheld relay device is used.

FIG. 1B is an illustrative view depicting another example of an in vivo analyte monitoring system 100B having a sensor control device 102, a handheld relay device 200, and one or more reader devices 120. At a high level, in vivo analyte monitoring system 100B is similar to that of system 100A (FIG. 1A), except that a handheld relay device 200 can be used to relay data indicative of the sensed analyte level received from sensor control device 102 to one or more reader devices 120. In certain embodiments, handheld relay device 200 can be configured to act as a hub to which sensor control device 102 can directly transmit data, and in turn, handheld relay device 200 can transmit the received data to one or more reader devices 120, which can be configured as endpoints. In this regard, a sensor control device 102 is not required to communicate directly with reader device 120 as previously shown in system 100A (FIG. 1A). Furthermore, sensor control device 102 can be configured to enter into a state in which it only accepts connection requests and data requests directly from handheld relay device 200. As described in further detail below, in situations where the sensor control device 102 and handheld relay device 200 are manufactured by the same entity, a proprietary communication protocol can also be used at communication path 143. In addition, the handheld relay device 200 may include a test strip interface 224 for receiving analyte test strips and performing in vitro analyte measurements, which in turn may be visually displayed on a display 222 of the handheld relay device, or transmitted to one or more reader devices 120.

For signal noise reduction, improved power management, enhanced security, interoperability, and other reasons, it may be advantageous to utilize a handheld relay device 200 to relay data wireless communications between sensor control device 102 and one or more reader devices 120 within the in vivo analyte monitoring system 100B of FIG. 1B.

In one aspect, handheld relay device 200 and sensor control device 102 can be configured to use advertising and connection schemes in a wireless LAN, for example, that are not supported by the operating systems of reader devices 120. For example, according to the Bluetooth Low Energy (BTLE) standard protocol, each BTLE device can be configured according to a set of connection parameters, including a connection interval maximum parameter. The connection interval maximum parameter can determine how often a BTLE controller device (e.g., handheld relay device 200) will ask for data from a BTLE peripheral device (e.g., sensor control device 102). According to the BTLE standard protocol, the connection interval must be between 7.5 milliseconds and 4 seconds. (See "Specification of the Bluetooth System, Covered Core Package version 4.2, Volume 6" at page 76-77 ("4.5.1 Connection Events").) Furthermore, third party manufacturers of reader devices may set their own requirements with regard to BTLE connection parameters. For example, for BTLE peripherals (e.g., sensor control devices 102) communicating with Apple iOS devices, the connection interval parameter must be equal to or less than 2 seconds.

In some embodiments, handheld relay device 200 can be configured to receive data transmissions from sensor control device 102 at a connection interval greater than the connection intervals allowed by mobile operating systems (e.g., iOS and Android) of reader devices 120, thereby reducing the number of times the radio transmitter of sensor control device 102 must turn on and off in a given period. This potentially reduces power consumption in sensor control device 102 and, moreover, can minimize signal noise interference from the radio transmitter, which can adversely impact sensitive analog sensor readings. By contrast, a handheld relay device 200 can be better suited for supporting multiple reader devices 120, because it can have a larger power supply than the sensor control device 102 for the operation of its wireless communication circuitry, as well as fewer concerns regarding signal noise interference.

In further embodiments, the in vivo analyte monitoring system of 100B allow for enhanced security and interoperability. For example, a proprietary wireless protocol may be used between the sensor control device 102 and the handheld relay device 200, increasing the likelihood that data indicative of a sensed analyte level is transmitted from the sensor control device 102 to a handheld relay device 200 in a secure and predictable manner. This can be advantageous because the sensor control device 102 may have limited power, memory (e.g., for storing instructions), and processing capability (e.g., for executing instructions). Use of a proprietary communication protocol can alleviate the need for the sensor control device 102 to accommodate for a variety of connection requirements attendant with the various operating systems (e.g., iOS, Android, Windows) of different reader devices, which can be taxing on a sensor control device 102 that may have limited resources.

Moreover, a proprietary communication protocol can offer improved security by mitigating the risk of "man-in-the-middle" attacks against the sensor control device 102 and a handheld relay device 200. For example, encryption keys can be generated and exchanged between sensor control device 102 and handheld relay device 200 during a typical pairing procedure in which a communication channel is established between the two devices. One of any number of key generation algorithms, which are known in the art, can be used to generate a private key and a corresponding public key. Examples of key generation algorithms that can be used include, but are not limited to RSA algorithms such as those described in the Public-Key Cryptography Standards (PKCS). Any desired key length can be used, but keys with longer lengths will typically provide more security. For example, key lengths of 128 bits, 256 bits, 512 bits, 1024 bits, 2048 bits, and 4096 bits, as well as others, can be used.

According to the proprietary communication protocol, however, upon completion of the key exchange, the communication channel can be closed and need not remain open. Subsequently, data indicative of a sensed analyte level can be encrypted by the sensor control device 102 using a private encryption key, and, in turn, decrypted by the handheld relay device 200 using a public encryption key. Accordingly, sensor control device 102 enters into a state in which it exclusively accepts data and connection requests from handheld relay device 200, and moreover, controls the timing interval of communications with handheld relay device 200.

This configuration can provide several advantages over prior modes of wireless communications in in vivo analyte monitoring systems, wherein handheld relay device 200 manages the timing intervals between communications. In those instances, where handheld relay device 200 manages the timing of communications, sensor control device 102 would be required to maintain and store previous data packets, to respond to requests from handheld relay device 200, while concurrently compiling new data packets from analyte measurement data from the analyte sensor. This can be disadvantageous in that sensor control device 102 would require more power, storage and processing resources. In addition, simultaneous transmission and analyte measurements can have undesirable effects, such as signal noise interference with the analyte sensor. By contrast, according to some embodiments of the present disclosure, in instances where sensor control device 102 manages the timing intervals between communications, sensor control device 102 can time the transmissions with handheld relay device 200 to coincide with periods in between analyte measurements. As such, sensor control device 102 can be optimized to use less power, storage and processing resources, as well as avoid signal noise interference.

Furthermore, in embodiments where sensor control device 102 manages the timing intervals between communications, handheld relay device 200 can discern the timing of the sensor control device 102 from information in the data packets. For example, sensor control device 102 can be configured to transmit data packets once per minute within a ten-second window. The precise time within the ten-second window at which the packet is sent can be determined by the packet number and the serial number of sensor control device 102. On initial connection with sensor control device 102, handheld relay device 200 can listen for a signal from sensor control device 102 for up to a minute. Upon receiving a first packet, handheld relay device 200 can analyze the packet number and serial number of sensor control device 102, and thus discern the data transmission timing of the next packet based on a known time-hopping algorithm. In other embodiments, sensor control device 102 can similarly provide life count and patch ID information according to a known time-hopping algorithm, such that the handheld relay device 200 can discern the timing of sensor control device 102 after receiving the first packet.

Data received by handheld relay device 200 can also be encrypted (in a similar manner described above with respect to data transmitted by the sensor control device 102) and stored in a memory 280 prior to transmission to one or more reader devices 120. Subsequently, data indicative of a sensed analyte level and the in vitro blood analyte measurements (e.g., test strip measurements) can be decrypted by the reader device 120 using a public encryption key and displayed to the user.

Another example of an advantage provided through the use of handheld relay device 200 can be increased interoperability. In particular, the frequent release of new or updated operating systems for reader devices 120 may necessitate an update to devices which interoperate with the reader devices. It can be advantageous to deploy new software and/or firmware to a handheld relay device 200, instead of the sensor control device 102, which may include an application-specific interface circuitry (ASIC) that cannot be easily reprogrammed.

Referring again to FIG. 1B, communications paths 143 and 144 between the devices shall be described in further detail. Sensor control device 102 and the handheld relay device 200 can communicate with each other over a local communication path (or link) 143, and handheld relay device 200 and one or more reader devices can communicate with each other over one or more local communication paths (or link) 144. Handheld relay device 200 can be configured to serve as a hub between the sensor control device 102 and one or more reader devices 120. In this regard, handheld relay device 200 can serve as a central device to accept and manage connections to endpoints (e.g., reader devices 120), as well as relay the sensed analyte data received from sensor control device 102. Communication paths 143 and/or 144 can each be uni-directional or bi-directional. In embodiments where paths 143 and/or 144 are wireless, a near field communication (NFC) protocol, RFID protocol, Bluetooth or Bluetooth Low Energy protocol, Wi-Fi protocol, proprietary protocol or the like can be used, including those communication protocols in existence as of the date of this filing or their later developed variants. In an alternative embodiment, communications paths 144 can be the same path, for example, via a broadcasting or multi-casting communication. Further, all communications over paths 143 and/or 144 can be encrypted, and sensor control device 102, handheld relay device 200, reader devices 120, remote computer system 170, and trusted computer system 180 can each be configured to encrypt and decrypt those communications sent and received.

As described above, a proprietary communication protocol can also be used at communication path 143, particularly in instances where the sensor control device 102 and the handheld relay device 200 are manufactured and/or supported by the same company. The proprietary communication protocol can be, for example, a variation of a standard wireless communication protocol, in which certain parameters can be configured with values which exceed a threshold minimum or maximum value in the standard protocol. As one example, for Bluetooth Low Energy devices, a connection interval maximum parameter can be implemented using a value that exceeds the 4 second maximum value that is set forth in the standard.

As shown in FIG. 1B, handheld relay device 200 can include a display 222 to output information to the user. For example, as depicted here, display 222 is outputting a current glucose level of 216 mg/dl. Handheld relay device 200 can also include an optional input component 221, such as a button, actuator, touch sensitive switch, capacitive switch, pressure sensitive switch, jog wheel or the like, to input data or commands to handheld relay device 200 or otherwise control the operation of handheld relay device 200. In certain embodiments, an output component of handheld relay device 200 includes a speaker (not shown) for outputting information as audible signals.

Handheld relay device 200 also includes one or more data communication ports 223 for wired data communication with external devices such as a remote terminal, e.g., a personal computer. Example data communication ports include USB ports, mini USB ports, USB Type-C ports, USB micro-A and/or micro-B ports, RS-232 ports, Ethernet ports, Firewire ports, or other similar data communication ports configured to connect to the compatible data cables. Handheld relay device 200 may also include an integrated or attachable in vitro glucose meter, including an in vitro test strip interface 224 to receive an in vitro glucose test strip for performing in vitro blood glucose measurements.

Referring still to FIG. 1B, display 222 can be configured to display a variety of information—some or all of which may be displayed at the same or different time on display 222. Display 222 may include, but is not limited to, providing a visual output of glucose values in real time or over a monitored time period; trend or directional arrow display that indicates a rate of analyte change and/or a rate of the rate of analyte change. Display 222 may also include a date display; a time of day display; a battery level indicator display; an impaired screen display; an audio/vibratory settings icon display; and a wireless connectivity status icon display for providing an indication of wireless communication connection with devices such as sensor control device 102 and reader device 120. In certain embodiments, display 222 of handheld relay device 200 has fewer functionalities relative to, for example, the display 122 of reader device 120. For example, as previously described, display 122 and input component 121 of reader device 120 may include a graphical display, a touch screen user interface, and/or other display and input features of smart phone devices. By contrast, display 222 of handheld relay device 200, having a relatively small form factor, can be limited to a numerical display (i.e., does not have a graphical user interface), as shown in FIG. 1B, and/or one or more directional arrows to indicate a trend and/or rate of analyte change.

In certain embodiments, handheld relay device 200 can be configured to output alarms, alert notifications, glucose values, etc., which may be visual, audible, tactile, or any combination thereof. Handheld relay device 200 may include other output components such as a speaker, vibratory output component and the like to provide audible and/or vibratory output indications to the user in addition to the visual output indication provided on display 222. For example, output unit 260 of handheld relay device 200 (FIG. 2B) can be adapted to progressively increase or decrease an associated auditory or vibratory signal over a predetermined time period in response to a monitored condition or event.

Handheld relay device 200 can be connected to one or more reader devices 120, which can be used by the user to display and/or analyze the collected analyte data. In turn, one or more reader devices 120, which can also be used by the user to display and/or analyze the collected data, can also be connected to a trusted computer system 180 that can be used for authentication of a third party software application or, as another example, for the storage of data indicative of a sensed analyte level. In both instances, handheld relay device 200 can function as a data conduit to transfer the stored analyte level information from the sensor control device 102 to one or more reader devices 120. In certain embodiments, the received data from the sensor control device 102 may be stored (permanently or temporarily) in one or more memories of handheld relay device 200.

Referring again to FIG. 1B, it is noted that, in addition to the features, functionalities and attributes described above with respect to the in vivo analyte monitoring system of 100B, the sensor control device 102, reader device 120, remote terminal 170, and trusted computer system 180, and each of the components included therewith, can each have any of the features, functionalities and attributes as described with respect to the in vivo analyte monitoring system of 100A (FIG. 1A). Furthermore, although two reader devices 120 are depicted, system 100B may comprise three, four, five or more similar or dissimilar reader devices 120. Similarly, system 100B can also comprise one reader device 120.

The processing of data within systems 100A and 100B can be performed by one or more control logic units or processors of the handheld relay device 200, one or more reader devices 120, remote terminal 170, trusted computer system 180, and/or sensor control device 102. For example, raw data measured by sensor 104 (after conversion to digital form) can be algorithmically processed into a value that represents the analyte level and that is readily suitable for display to the user, and this can occur in sensor control device 102, handheld relay device 200, reader device 120, remote terminal 170, or trusted computer system 180. This algorithmic processing can include the calibration of the raw data, the application of environmental compensation (e.g., temperature-based adjustments), the application of a proprietary algorithm, and the like. The information derived from the raw data can be displayed in any of the manners described above on any display of handheld relay device 200, reader device 120, remote terminal 170, or trusted computer system 180.

The information may be utilized by the user to determine any necessary corrective actions to ensure the analyte level remains within an acceptable and/or clinically safe range. Other visual indicators, including colors, flashing, fading, etc., as well as audio indicators, including a change in pitch, volume, or tone of an audio output, and/or vibratory or other tactile indicators may also be incorporated into the outputting of trend data as means of notifying the user of the current level, direction, and/or rate of change of the monitored analyte level. For example, based on a determined rate of glucose change, programmed clinically significant glucose threshold levels (e.g., hyperglycemic and/or hypoglycemic levels), and current analyte level derived by an in vivo analyte sensor, an algorithm stored on a computer readable medium of systems 100A and 100B can be used to determine the time it will take to reach a clinically significant level and can be used to output a notification in advance of reaching the clinically significant level, e.g., 30 minutes before a clinically significant level is anticipated, and/or 20 minutes, and/or 10 minutes, and/or 5 minutes, and/or 3 minutes, and/or 1 minute, and so on, with outputs increasing in intensity or the like.

Example Embodiments of Reader Devices

Figure 2A:
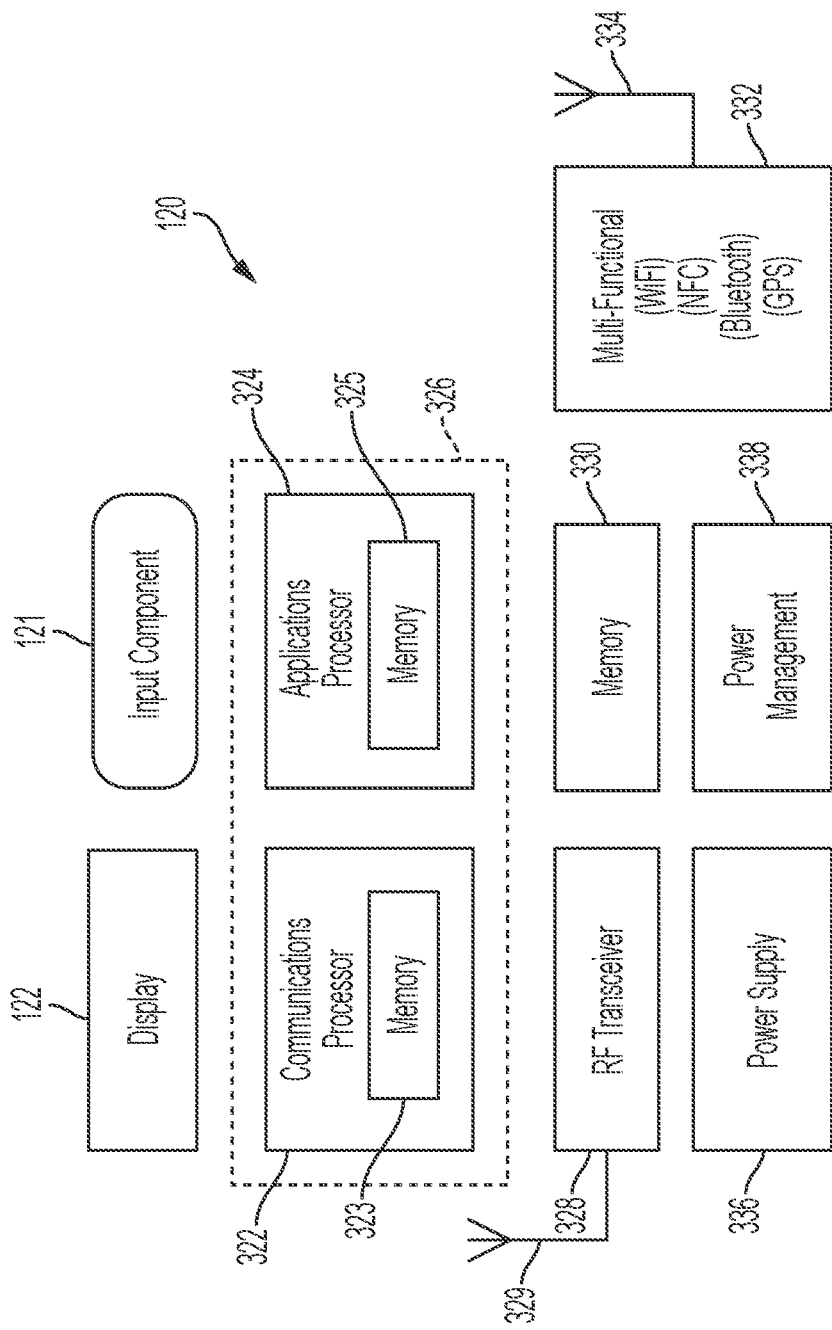
FIG. 2A is a block diagram depicting an example embodiment of a reader device.

FIG. 2A is a block diagram of an example embodiment of a reader device 120 configured as a smart phone. Here, reader device 120 includes an input component 121, display 122, and processing hardware 326, which can include one or more processors, microprocessors, controllers, and/or microcontrollers, each of which can be a discrete chip or distributed amongst (and a portion of) a number of different chips. Here, processing hardware 326 includes a communications processor 322 having on-board memory 323 and an applications processor 324 having on-board memory 325. Reader device 120 further includes an RF transceiver 328 coupled with an RF antenna 329, a memory 330, multi-functional circuitry 332 with one or more associated antennas 334, a power supply 336, and power management circuitry 338. FIG. 2A is an abbreviated representation of the typical hardware and functionality that resides within a smart phone and those of ordinary skill in the art will readily recognize that other hardware and functionality (e.g., codecs, drivers, glue logic), can also be included.

Communications processor 322 can interface with RF transceiver 328 and perform analog-to-digital conversions, encoding and decoding, digital signal processing and other functions that facilitate the conversion of voice, video, and data signals into a format (e.g., in-phase and quadrature) suitable for provision to RF transceiver 328, which can then transmit the signals wirelessly. Communications processor 322 can also interface with RF transceiver 328 to perform the reverse functions necessary to receive a wireless transmission and convert it into digital data, voice, and video.

Applications processor 324 can be adapted to execute the operating system and any software applications that reside on reader device 120, process video and graphics, and perform those other functions not related to the processing of communications transmitted and received over RF antenna 329. The smart phone operating system will operate in conjunction with a number of applications on reader device 120. Any number of applications (also known as "user interface applications") can be running on reader device 120 at any one time, and will typically include one or more applications that are related to a diabetes monitoring regime, in addition to the other commonly used applications that are unrelated to such a regime, e.g., email, calendar, weather, sports, games, etc. For example, the data indicative of a sensed analyte level and in vitro blood analyte measurements received by the reader device can be securely communicated to user interface applications residing in memory 325 of the reader device 120. Such communications can be securely performed, for example, through the use of mobile application containerization or wrapping technologies.

Memory 330 can be shared by one or more the various functional units present within reader device 120, or can be distributed amongst two or more of them (e.g., as separate memories present within different chips). Memory 330 can also be a separate chip of its own. Memory 330 is non-transitory, and can be volatile (e.g., RAM, etc.) and/or non-volatile memory (e.g., ROM, flash memory, F-RAM, etc.).

Multi-functional circuitry 332 can be implemented as one or more chips and/or components (e.g., transmitter, receiver, transceiver, and/or other communication circuitry) that perform other functions such as local wireless communications (e.g., for Wi-Fi, Bluetooth, Bluetooth Low Energy, Near Field Communication (NFC), Radio Frequency Identification (RFID), and others) and determining the geographic position of reader device 120 (e.g., global positioning system (GPS) hardware). One or more other antennas 334 are associated with the functional circuitry 332 as needed to operate with the various protocols and circuits.

Power supply 336 can include one or more batteries, which can be rechargeable or single-use disposable batteries. Power management circuitry 338 can regulate battery charging and power supply monitoring, boost power, perform DC conversions, and the like.

As mentioned, the reader device 120 may also include one or more data communication ports, such as USB ports, mini USB ports, USB Type-C ports, USB micro-A and/or micro-B ports, RS-232 ports, or any other wired communication ports for data communication with a handheld relay device 200, remote terminal 170, trusted computer system 180, or sensor control device 102, to name a few.

In further embodiments, reader devices 120 can be configured to receive data wirelessly over communication links 140, 144 from sensor control device 102 or handheld relay device 200. For example, the wireless communication circuitry 328, 334 of reader device 120 can be adapted to receive data indicative of a sensed analyte level, including a current analyte level, such as real-time analyte level information, historical analyte levels, a rate of change of an analyte level over a predetermined time period, and a rate of the rate of change of an analyte level. One or more processors 322, 324 can be configured to convert the received data indicative of a sensed level into a user readable form. The converted data can be communicated to the display 122 for outputting information to the user in the form of one or more visual, auditory or vibratory signals.

In still a further embodiment, the user using in vivo analyte monitoring system 100A or 100B (FIG. 1A or 1B) may manually input the blood glucose values using, for example, a user interface (for example, a keyboard, keypad, and the like) incorporated in reader device 120. In the alternative, a user may manually input blood glucose values using, for example, a user interface incorporated in the handheld relay device 120 or a remote terminal 170.

Example Embodiments of Handheld Relay Devices

Figure 2B:
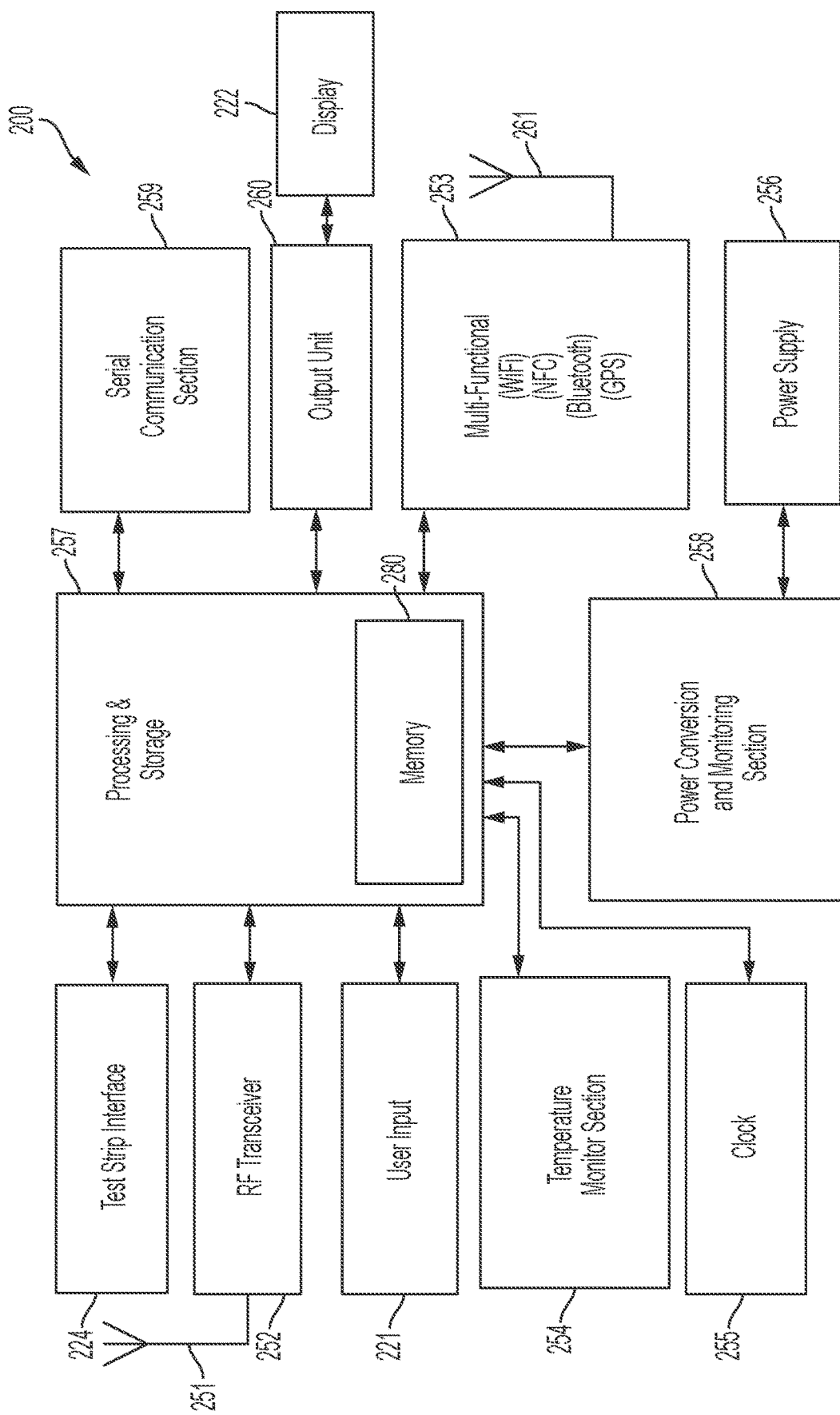
FIG. 2B is a block diagram depicting an example embodiment of a handheld relay device.

FIG. 2B is a block schematic diagram depicting a handheld relay device 200, as shown in FIG. 1B, in accordance with one embodiment of the present disclosure. Referring to FIG. 2B, the handheld relay device 200 includes an analyte test strip interface 224, an RF transceiver 252, a user input 221, a temperature detection section 254, and a clock 255, each of which is operatively coupled to one or more processors 257. As can be further seen from the Figure, the handheld relay device 200 also includes a power supply 256 operatively coupled to a power conversion and monitoring section 258. Further, the power conversion and monitoring section 258 is also coupled to the one or more processors 257 of the handheld relay device 200. Moreover, also shown are a serial communication section 259, and an output unit 260, each operatively coupled to the one or more processors 257.

In one embodiment, the test strip interface 224 includes a test strip port adapted to receive a manual insertion of in vitro test strips and perform in vitro blood analyte measurements. The test strip can be used to perform an in vitro measurement of a user's glucose level. Those of ordinary skill in the art will appreciate that in vitro measurements of other analytes (e.g., ketones, lactate, hemoglobin A1C or the like) are within the scope of the present disclosure. In such a configuration, handheld relay device 200 can process a fluid sample on a test strip, determine an analyte level contained therein, and display that result to a user. Various types of in vitro test strips can be suitable for use with handheld relay device 200. As a non-limiting example, test strips may be employed that only require a very small amount (e.g., one microliter or less, e.g., about 0.5 microliter or less, e.g., about 0.1 microliter or less) of applied sample to the strip in order to obtain accurate glucose information, e.g. FreeStyle® or Precision® blood glucose test strips and systems from Abbott Diabetes Care Inc. Handheld relay devices 200 with in vitro monitors and test strip ports may be configured to conduct in vitro analyte monitoring with no user calibration in vitro test strips (i.e., no human intervention calibration), such as FreeStyle Lite glucose test strips from Abbott Diabetes Care Inc. Detailed description of such test strips and devices for conducting in vitro analyte monitoring is provided in U.S. Pat. Nos. 6,377,894, 6,616,819, 7,749,740, 7,418,285; U.S. Patent Publication Nos. 2004/0118704, 2006/0091006, 2008/0066305, 2008/0267823, 2010/0094110, 2010/0094111, and 2010/0094112, and 2011/0184264, the disclosure of each of which are incorporated herein by reference for all purposes.

The in vitro analyte measurements can be communicated to the output unit 260 for visually displaying on the display 222 of handheld relay device 200, stored in non-volatile memory 280, or transmitted by the RF transceiver 252 or multi-functional circuitry 253 to another device, e.g., one or more reader devices 120. This manual testing of glucose can be used, for example, to calibrate sensor control unit 102 (shown in FIG. 1B).

In one embodiment, the RF transceiver 252 can be configured to communicate, via the communication links 143 and 144 (shown in FIG. 1B) with the communication circuitry 168 (shown in FIGS. 2C and 2D) of the sensor control device 102 or the RF transceivers of the one or more reader devices 120, to transmit and/or receive encoded data signals from the communication circuitry 168 (shown in FIGS. 2C and 2D) for, among others, signal mixing, demodulation, and other data processing. One or more antennas 251 are associated with RF transceiver 252 as needed to operate with the various protocols and circuits.

Multi-functional circuitry 253 can be implemented as one or more chips and/or components (e.g., transmitter, receiver, transceiver, and/or other communication circuitry) that perform other functions such as local wireless communications (e.g., for Wi-Fi, Bluetooth, Bluetooth Low Energy, Near Field Communication (NFC), Radio Frequency Identification (RFID), and others) and determining the geographic position of handheld relay device 200 (e.g., global positioning system (GPS) hardware). In certain embodiments, however, the wireless communication circuitry of handheld relay device 200 is limited in functionality, relative to reader device 120, for example, in that it does not include native Global System Mobile Communications (GSM) or Code Division Multiple Access (CDMA) functionality. In one embodiment, the multi-functional circuitry 253 can be configured to communicate, via the communication links 143 and 144 (FIG. 1B) with the communication circuitry 168 (shown in FIGS. 2C and 2D) of the sensor control device 102 and the RF transceivers of the one or more reader devices 120, to transmit and/or receive encoded data signals from the communication circuitry 168 (shown in FIGS. 2C and 2D) for, among others, signal mixing, demodulation, and other data processing. One or more antennas 261 are associated with the functional circuitry 253 as needed to operate with the various protocols and circuits.

In a further embodiment, the handheld relay device 200 can be configured to receive data wirelessly over communication link 143 from sensor control device 102. For example, wireless communication circuitry 252, 253 of handheld relay device 200 can be adapted to receive data indicative of a sensed analyte level, including a current analyte level, such as real-time analyte level information, historical analyte levels, a rate of change of an analyte level over a predetermined time period, and a rate of the rate of change of an analyte level. One or more processors 257 can be configured to convert the received data indicative of a sensed level into a user readable form. The one or more processors 257 can also be configured to convert in vitro analyte measurements performed by the test strip interface 224 into a user readable format. The converted data and measurements can be communicated to the output unit 260 for outputting information to the user in the form of one or more visual, auditory or vibratory signals.

The input device 221 of the handheld relay device 200 is configured to allow the user to enter information into the handheld relay device 200 as needed. The temperature detection section 254 is configured to provide temperature information of the handheld relay device 200 to the one or more processors 257, while the clock 255 provides, among others, real time information to the one or more processors 257. Furthermore, the input device 221 of the handheld relay device 200 is limited in functionality, relative to the reader device 120, and does not include a microphone or other voice-input functionalities.

Each of the various components of the handheld relay device 200 shown in FIG. 2B is powered by the power supply 256 which can include a battery. The battery can be a disposable, one-time use battery or a rechargeable battery (e.g., nickel-cadmium (NiCd), nickel-zinc (NiZn), nickel metal hydride (NiMH), lithium-ion (Li-ion)) that may be recharged by a separate power supply recharging unit (not shown). Furthermore, the power conversion and monitoring section 258 is configured to monitor the power usage by the various components in the handheld relay device 200 for effective power management and to alert the user, for example, in the event of power usage which renders the handheld relay device 200 in sub-optimal operating conditions. An example of such sub-optimal operating condition may include, for example, operating the vibration output mode (as discussed below) for a period of time thus substantially draining the power supply 256 while the one or more processors 257 (thus, the handheld relay device 200) is turned on. Moreover, the power conversion and monitoring section 258 may additionally be configured to include a reverse polarity protection circuit such as a field effect transistor (FET) configured as a battery activated switch.

The serial communication section 259 in the handheld relay device 200 is configured to provide a bi-directional communication path from the testing and/or manufacturing equipment for, among others, initialization, testing, and configuration of the handheld relay device 200. Serial communication section 259 can also be used to upload data to a computer, such as time-stamped blood glucose data. The communication link with an external device (not shown) can be made, for example, by cable, infrared (IR) or RF link.

The output unit 260 of the handheld relay device 200 is coupled to display 222 and can provide, for example, numerical information for display to a user (e.g., a current glucose level). Additionally, output unit 260 may also include an integrated speaker for outputting audible signals as well as to provide vibration output as commonly found in handheld electronic devices, such as mobile telephones presently available. In a further embodiment, the handheld relay device 200 also includes an electro-luminescent lamp configured to provide backlighting to the output unit 260 for visual display in dark ambient surroundings.

Referring back to FIG. 2B, the handheld relay device 200 in one embodiment may also include a storage section such as a programmable, non-volatile memory device 280 as part of the one or more processors 257 (as shown here), or provided separately in the handheld relay device 200, operatively coupled to the one or more processor 257. The one or more processors 257 can be further configured to perform Manchester decoding, as well as error detection and correction upon the encoded data signals received from the sensor control unit 102 via the communication link 143.

Example Embodiments of Monitoring, Alarming and Reporting Routines

In some embodiments, monitoring, alarming and reporting routines can be stored in memory and executed by one or more processors of the handheld relay device 200 or a reader device 120. For example, a monitoring routine, stored in memory 280 of handheld relay device 200, can be executed by one or more processors 257 to monitor the state of the wireless connections between handheld relay device 200 and the sensor control device 102. The monitoring routine can further include a command to output a visual, audio or vibratory alarm in response to a loss of wireless connectivity with the sensor control device 102. In some embodiments, for example, a monitoring routine can include the transmission of an alarm command from a handheld relay device 200 to a reader device 120.

Similarly, monitoring routines for failure conditions can be stored in memory of the handheld relay device 200 or the one or more reader devices 120. As described earlier, the sensor control device 102 and handheld relay device 200 may be manufactured and/or sold by the same company. By contrast, reader devices 120 (e.g., smartphone) can be manufactured by various third parties, and may also include any number of third party user interface applications. Thus, because the manufacturer of the handheld relay device 200 may have more control over its own devices, in some embodiments, the failure condition monitoring routines of the handheld relay device 200 can be configured with a greater degree of rigor than the failure condition monitoring routines of the reader device 120. The heightened rigor for the failure condition monitoring routines on a handheld relay device 200 can comprise, for example, an increased rate of monitoring, the use of background application processing, and/or the use and prioritization of multithreaded applications. Handheld relay device 200 can be configured by a manufacturer, for example, to provide a higher degree of priority for failure condition monitoring routines, in terms of memory allocation, processor usage, display usage and/or network bandwidth. By comparison, the degree of rigor (i.e., local prioritization) for failure condition monitoring routines on a reader device 120 (e.g., smartphone), whose primary function may not be as a medical device, may be constrained by the mobile operating system and/or other third-party user interface applications. A failure condition monitoring routine on a reader device 120, for example, may be placed into background processing, or in a low-priority processing state, due to the presence of other third-party user interface applications. Similarly, the failure condition monitoring routine may enter into a suspended state and/or be unable to execute at all until it is returned to the foreground. In addition, reader devices 120 may not be capable of prioritizing displayable events and/or allocating reserved network bandwidth for failure condition monitoring routines.

In some embodiments, the failure condition monitoring routine can further include a command to execute one or more predetermined fail-safe procedures in response to the detection of one or more failure conditions. Optionally, the failure conditions and fail-safe procedures may be configurable by a user of handheld relay device 200, and may further require that the user input a passcode through the user input device 221 to confirm any changes thereto.

Figure 3:
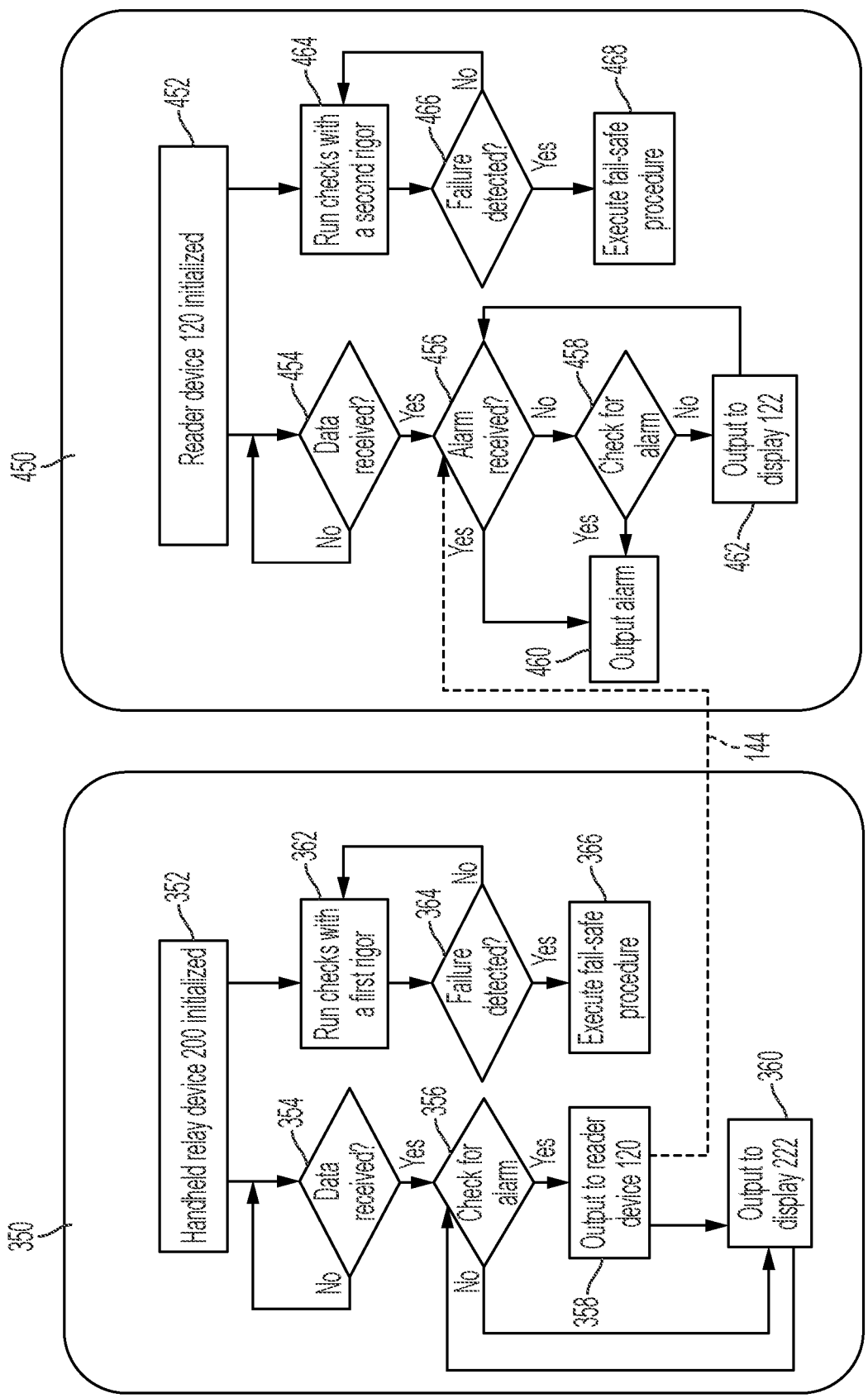
FIG. 3 is a flow diagram depicting example embodiments of methods for monitoring and alarming in a handheld relay device.

FIG. 3 is a flowchart diagram showing one embodiment of multiple monitoring and alarming routines 350, 450 for a handheld relay device 200 and a reader device 120. Turning to the handheld relay device 200, multiple monitoring and alarming routines 350 are stored in memory 280 and executed by one or more processors 257. At Step 352, handheld relay device 200 is initialized, for example, by powering on or power cycling the device. At Step 354, handheld relay device 200 periodically performs a check to confirm that it has received data, e.g., data indicative of a sensed analyte level, from sensor control device 102.

At Step 356, handheld relay device 200 evaluates the received data and the state of the handheld relay device 200 for the occurrence of one or more predetermined alarm conditions. In some embodiments, for example, predetermined alarm conditions may include the detection of a hypoglycemic or hyperglycemic condition, as determined from the sensed analyte data received from the sensor control device 102 or the in vitro analyte measurements determined for a test sample received through a test strip port; the power reserve of the handheld relay device 200; and the wireless connectivity between handheld relay device 200 and sensor control device 102. For example, a battery indicator icon on the display 222 of the handheld relay device 200 may indicate the approximate amount of power left in the device. If no predetermined alarm conditions are determined, handheld relay device 200 can output a signal to the display indicating a normal status, or in the alternative, no output is sent to the display at all. If one or more predetermined alarm conditions are determined, at Step 358, the handheld relay device 200 can output an alarm to the reader device 120 over communication path 144. Further, at Step 360, the handheld relay device 200 can also output an alarm to the local display, for example, and can also generate an auditory or vibratory signal. As seen in FIG. 3, the monitoring and alarming routine 350 can return to Step 356 to continue checking for predetermined alarm conditions.

In some embodiments, the handheld relay device 200 can concurrently execute, by its one or more processors 257, instructions stored in memory 280 for the monitoring of failure conditions. Referring again to the monitoring and alarming routines 350 in FIG. 3, at Step 362, the handheld relay device 200 can periodically perform checks for one or more predetermined failure conditions at a first rigor. In some embodiments, for example, the predetermined failure conditions can include monitoring for an impaired display condition, a low power condition, a low data storage condition and a network communication failure condition. At Step 364, handheld relay device 200 determines if one or more predetermined failure conditions has occurred. If so, handheld relay device 200 can perform one or more fail-safe procedures at Step 366. In some embodiments, the fail-safe procedures can include one or more of power cycling handheld relay device 200, powering off handheld relay device 200, resetting handheld relay device 200 to factory default settings and outputting a visual notification to the display 222 of handheld relay device. If no failure conditions are determined, the routine can return to Step 362 to continue monitoring for failure conditions at a first rigor.

Monitoring and alarm routines 450 can also be stored in a memory 325, 330 and executed by one or more processors 324 of the one or more reader devices 120. Referring again to FIG. 3, at Step 452, reader device 120 is initialized, for example, by powering on or power cycling the device. At Step 454, reader device 120 periodically performs a check to confirm that it has received data from the handheld relay device 200, which can include, for example, data indicative of a sensed analyte level. At Step 456, the monitoring routine can also determine if a command to output an alarm has been received from the handheld relay device 200, as previously described at Step 358. If an alarm command is received, then the reader device 120 can output an alarm at Step 460. If an alarm command has not been received, then at Step 458, the reader device 120 checks for the occurrence of one or more predetermined alarm conditions, which may comprise any of the alarm conditions described above with respect to the handheld relay device 200. If an alarm condition is detected, then the reader device 120 can output an alarm at Step 460. If an alarm condition is not detected, then the reader device can output an indication to the display 122 that the current status is normal, or in the alternative, take no action and return to Step 456 to continue monitoring for alarm commands and conditions.

In further embodiments, the reader device 120 can concurrently execute, by its one or more processors 324, instructions stored in memory 325, 330 for the monitoring of failure conditions. At Step 464, reader device 120 can periodically perform checks for one or more predetermined failure conditions at a second rigor. As described earlier, in some embodiments, the degree of rigor for failure condition monitoring in the reader device 120 is lower than the degree of rigor for failure condition monitoring in the handheld relay device 200. At Step 466, the reader device 120 determines if one or more predetermined failure conditions has occurred. If so, the reader device 120 can perform one or more fail-safe procedures at Step 468. It should be understood that the predetermined failure conditions and fail-safe procedures in the reader device 120 can include one or more of the same failure conditions and fail-safe procedures described above with respect to the handheld relay device 200. If no failure conditions are determined, the routine can return to Step 464 to continue monitoring for failure conditions at a second rigor.

In certain embodiments, reader device 120 can also be configured to store and retrieve data indicative of a sensed analyte level and in vitro blood analyte measurements, for the creation of reports. For example, a user of reader device 120 can use a user interface to choose a report from a plurality of selectable report formats. One or more processors 324 of reader device 120 can then retrieve at least a subset of the data indicative of the sensed analyte level and the in vitro blood analyte measurements based on the user's selection, organize the retrieved data, and output the selected report to display 122 of reader device 120.

Example Embodiments of Sensor Control Devices

Figure 2C:
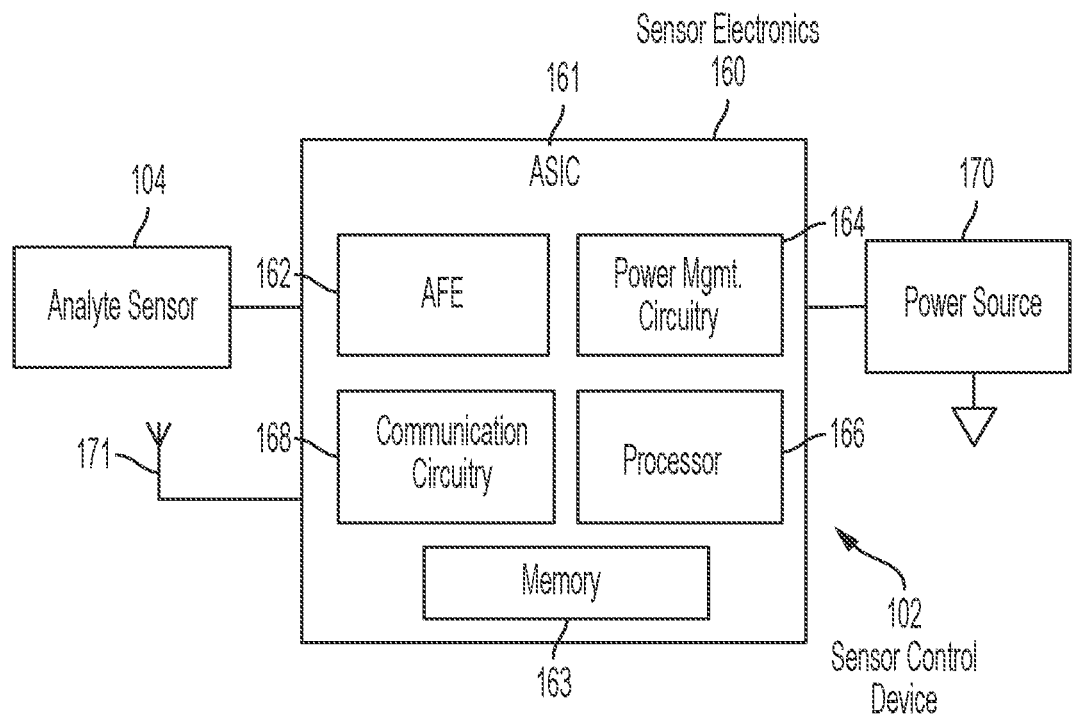
FIGS. 2C-D are block diagrams depicting example embodiments of a sensor control device.
Figure 2D:
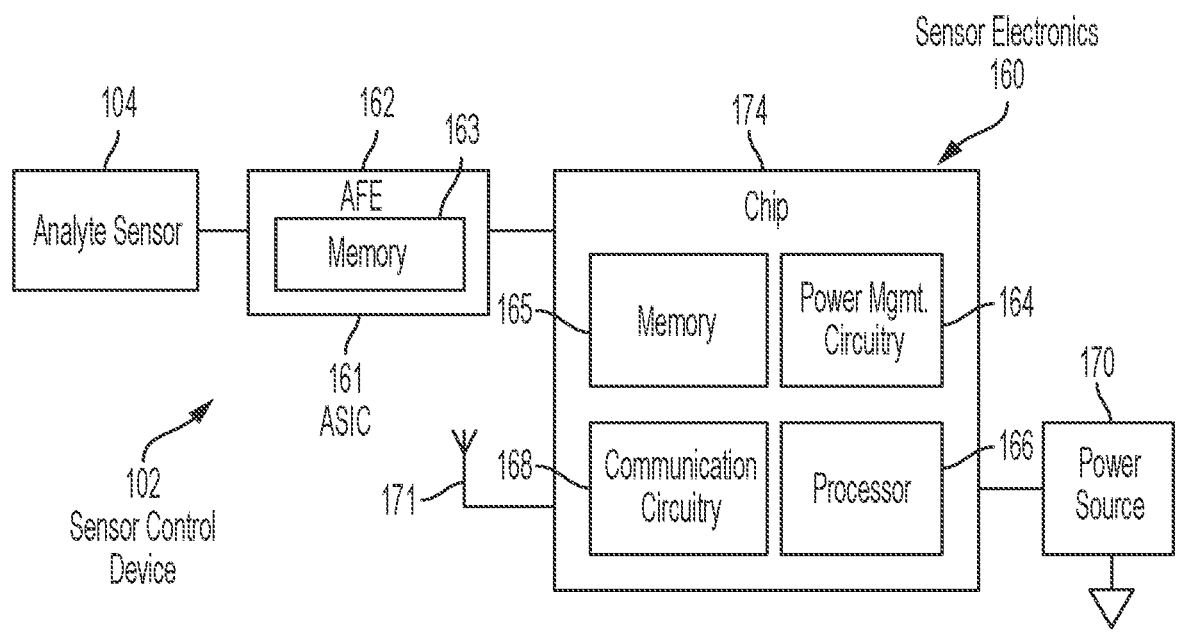

FIGS. 2C-D are block schematic diagrams depicting example embodiments of sensor control device 102 having analyte sensor 104 and sensor electronics 160 (including analyte monitoring circuitry) that can have the majority of the processing capability for rendering end-result data suitable for display to the user. In FIG. 2C, a single semiconductor chip 161 is depicted that can be a custom application specific integrated circuit (ASIC). Shown within ASIC 161 are certain high-level functional units, including an analog front end (AFE) 162, power management (or control) circuitry 164, processor 166, and communication circuitry 168 (which can be implemented as a transmitter, receiver, transceiver, passive circuit, or otherwise according to the communication protocol). In this embodiment, both AFE 162 and processor 166 are used as analyte monitoring circuitry, but in other embodiments either circuit can perform the analyte monitoring function. Processor 166 can include one or more processors, microprocessors, controllers, and/or microcontrollers, each of which can be a discrete chip or distributed amongst (and a portion of) a number of different chips.

A memory 163 is also included within ASIC 161 and can be shared by the various functional units present within ASIC 161, or can be distributed amongst two or more of them. Memory 163 can also be a separate chip. Memory 163 can be volatile and/or non-volatile memory. In this embodiment, ASIC 161 is coupled with power source 170, which can be a coin cell battery, or the like. AFE 162 interfaces with in vivo analyte sensor 104 and receives measurement data therefrom and outputs the data to processor 166 in digital form, which in turn processes the data to arrive at the end-result glucose discrete and trend values, etc. This data can then be provided to communication circuitry 168 for sending, by way of antenna 171, to handheld relay device 200 (not shown), for example, where minimal further processing is needed by the resident software application to display the data.

FIG. 2D is similar to FIG. 2C but instead includes two discrete semiconductor chips 162 and 174, which can be packaged together or separately. Here, AFE 162 is resident on ASIC 161. Processor 166 is integrated with power management circuitry 164 and communication circuitry 168 on chip 174. AFE 162 includes memory 163 and chip 174 includes memory 165, which can be isolated or distributed within. In one example embodiment, AFE 162 is combined with power management circuitry 164 and processor 166 on one chip, while communication circuitry 168 is on a separate chip. In another example embodiment, both AFE 162 and communication circuitry 168 are on one chip, and processor 166 and power management circuitry 164 are on another chip. It should be noted that other chip combinations are possible, including three or more chips, each bearing responsibility for the separate functions described, or sharing one or more functions for fail-safe redundancy.

Performance of the data processing functions within the electronics of the sensor control device 102 provides the flexibility for systems 100A and 100B to schedule communication from sensor control device 102 to one or more reader devices 120 or handheld relay device 200, which in turn limits the number of unnecessary communications and can provide further power savings at sensor control device 102.

Information may be communicated from sensor control device 102 to one or more reader devices 120 or handheld relay device 200 automatically and/or continuously when the analyte information is available, or may not be communicated automatically and/or continuously, but rather stored or logged in a memory of sensor control device 102, e.g., for later output. In another embodiment, information, including data indicative of a sensed analyte level, may be stored or logged in a memory of handheld relay device 200 and/or one or more reader devices 120. Accordingly, in many embodiments of systems 100A and 100B, analyte information derived by sensor control device 102 is made available in a user-usable or viewable form only when queried by the user such that the timing of data communication is selected by the user.

Data can be sent from sensor control device 102 to handheld relay device 200 and/or one or more reader devices 120 at the initiative of either sensor control device 102, handheld relay device 200 or one or more reader devices 120. For example, in some example embodiments sensor control device 102 can communicate data periodically in a broadcast-type fashion, such that an eligible handheld relay device 200, if in range and in a listening state, can receive the communicated data (e.g., sensed analyte data). This is at the initiative of sensor control device 102 because handheld relay device 200 does not have to send a request or other transmission that first prompts sensor control device 102 to communicate. Broadcasts can be performed, for example, using an active Wi-Fi, Bluetooth, or BTLE connection. The broadcasts can occur according to a schedule that is programmed within sensor control device 102 (e.g., about every 1 minute, about every 5 minutes, about every 10 minutes, or the like). Broadcasts can also occur in a random or pseudorandom fashion, such as whenever sensor control device 102 detects a change in the sensed analyte data. Further, broadcasts can occur in a repeated fashion regardless of whether each broadcast is actually received by handheld relay device 200.

Systems 100A and 100B can also be configured such that the handheld relay device 200 sends a transmission that prompts sensor control device 102 to communicate its data to the handheld relay device 200. Similarly, systems 100A and 100B can also be configured such that one or more reader devices 120 send a transmission that prompts handheld relay device 200 to communicate its data to the one or more reader devices 120. This is generally referred to as "on-demand" data transfer. An on-demand data transfer can be initiated based on a schedule stored in the memory of the handheld relay device 200 or the one or more reader devices 120, or at the behest of the user via a user interface of the handheld relay device 200 or the one or more reader devices 120. For example, if the user wants to check his or her analyte level, the user could perform a scan of sensor control device 102 using an NFC, Bluetooth, BTLE, proprietary protocol or Wi-Fi connection. Data exchange can be accomplished using broadcasts only, on-demand transfers only, or any combination thereof.

Accordingly, once a sensor control device 102 is placed on the body so that at least a portion of sensor 104 is in contact with the bodily fluid and electrically coupled to the electronics within device 102, sensor derived analyte information may be communicated in on-demand or broadcast fashion from sensor control device 102 to handheld relay device 200 or one or more reader devices 120. On-demand transfer can occur by first powering on handheld relay device 200 or one or more reader devices 120 (or they may be continually powered) and executing a software algorithm stored in and accessed from a memory of handheld relay device 200 or one or more reader devices 120 to generate one or more requests, commands, control signals, or data packets to send to sensor control device 102. The software algorithm executed under, for example, the control of processing hardware 257 of handheld relay device 200 may include routines to detect the position of the sensor control device 102 relative to handheld relay device 200 to initiate the transmission of the generated request command, control signal and/or data packet.

Different types and/or forms and/or amounts of information may be sent as part of each on-demand or other transmission including, but not limited to, one or more of current analyte level information (i.e., real time or the most recently obtained analyte level information temporally corresponding to the time the reading is initiated), rate of change of an analyte over a predetermined time period, rate of the rate of change of an analyte (acceleration in the rate of change), or historical analyte information corresponding to analyte information obtained prior to a given reading and stored in a memory of sensor control device 102.

Some or all of real time, historical, rate of change, rate of rate of change (such as acceleration or deceleration) information may be sent to handheld relay device 200 or one or more reader devices 120 in a given communication or transmission. In certain embodiments, the type and/or form and/or amount of information sent to handheld relay device 200 or one or more reader devices 120 may be preprogrammed and/or unchangeable (e.g., preset at manufacturing), or may not be preprogrammed and/or unchangeable so that it may be selectable and/or changeable in the field one or more times (e.g., by activating a switch of the system, etc.). Accordingly, in certain embodiments, handheld relay device 200 or one or more reader device 120 can output a current (real time) sensor-derived analyte value (e.g., in numerical format), a current rate of analyte change (e.g., in the form of an analyte rate indicator such as an arrow pointing in a direction to indicate the current rate), and analyte trend history data based on sensor readings acquired by and stored in memory of sensor control device 102 (e.g., in the form of a graphical trace). Additionally, an on-skin or sensor temperature reading or measurement may be communicated from sensor control device 102 with each data communication. The temperature reading or measurement, however, may be used in conjunction with a software routine executed by handheld relay device 200 to correct or compensate the analyte measurement output to the user by handheld relay device 200, instead of or in addition to actually displaying the temperature measurement to the user.

U.S. Patent Publ. No. 2011/0213225 (the '225 Publication) generally describes components of an in vivo-based analyte monitoring system that are suitable for use with the authentication methods and hardware embodiments described herein. The '225 Publication is incorporated by reference herein in its entirety for all purposes. For other examples of sensor control device 102 and reader device 120, see, e.g., devices 102 and 120, respectively, as described in the incorporated '225 Publication.

Additional detailed description of the analyte monitoring system, and its various components including the functional descriptions of the transceivers are provided in U.S. Pat. No. 6,175,752 issued Jan. 16, 2001, entitled "Analyte Monitoring Device and Methods of Use", and in U.S. patent application Ser. No. 10/745,878 filed Dec. 26, 2003, now U.S. Pat. No. 7,811,231, entitled "Continuous Glucose Monitoring System and Methods of Use", each assigned to the Assignee of the present application, and each of which are incorporated herein by reference for all purposes.

Example Embodiments for Wireless Communication in In Vivo Analyte Monitoring Systems In all of the embodiments described herein, communications between sensor control device 102 and handheld relay device 200 (as shown in FIG. 1B), can occur wirelessly using a Bluetooth, Bluetooth Low Energy (BTLE) or proprietary wireless protocol. Communications between handheld relay device 200 and reader device 120 (as shown in FIG. 1B), or between sensor control device 102 and reader device 120 (as shown in FIG. 1A), can occur wirelessly using a Bluetooth or Bluetooth Low Energy (BTLE) standard protocol. Further described below are example embodiments of Bluetooth and BTLE topologies and advertising schemes for use with in vivo analyte monitoring systems, like those described above and depicted in FIGS. 1A and 1B.

Figure 4A:
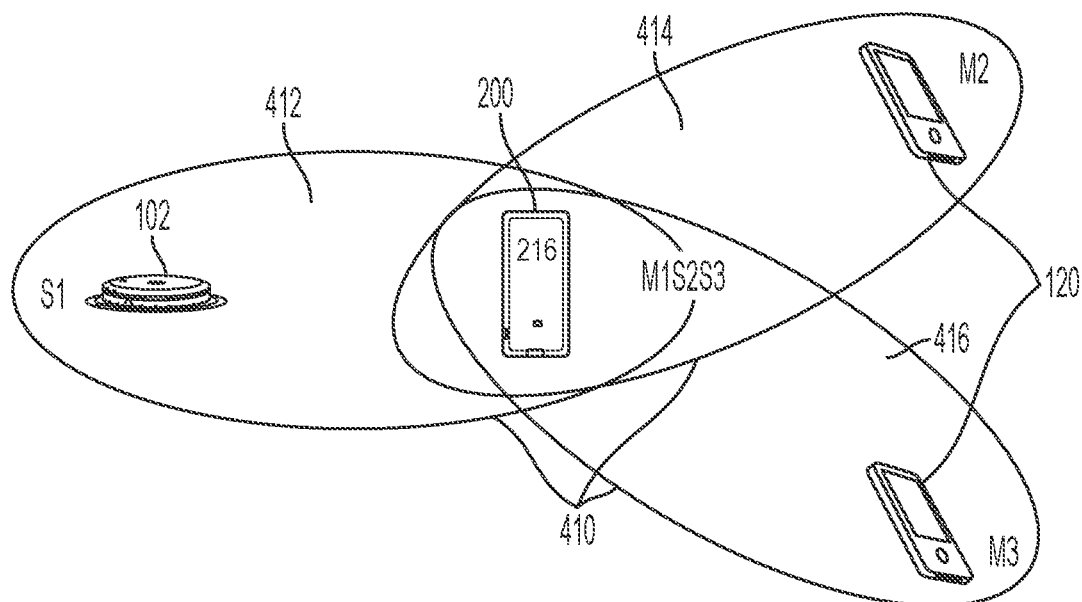
FIGS. 4A-B are topology diagrams depicting examples of wireless network topologies for use with an in vivo analyte monitoring system.
Figure 4B:
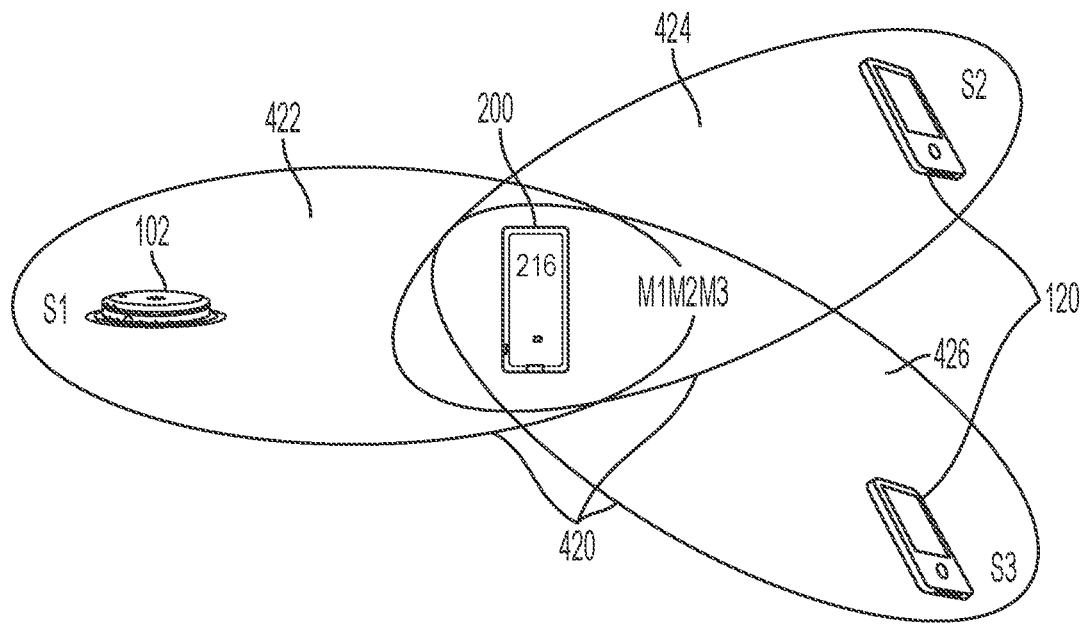

FIGS. 4A and 4B are diagrams showing example topologies for use with in vivo analyte monitoring systems, in which one or more devices communicate through a Bluetooth or BTLE protocol. Bluetooth and BTLE devices can communicate with each other in a piconet, which can comprise two or more devices occupying the same channel (or different channels), and synchronized to a common clock. FIG. 4A depicts an example embodiment of a BTLE topology with sensor control device 102, handheld relay device 200, and reader devices 120 configured as a single BTLE piconet 410 comprising three channels 412, 414, and 416. In this embodiment, sensor control device 102 can be configured as a slave device (S1) relative to handheld relay device 200, and handheld relay device 200 can be configured as a master device (M1) relative to sensor control device 102. Reader devices 120 can each be configured as master devices (M2, M3) relative to handheld relay device 200, and handheld relay device 200 can be configured as a slave device (S2, S3) to reader devices 120.

Furthermore, in this embodiment, sensor control device 102 can communicate with handheld relay device 200 over an advertising channel or a piconet physical channel. For example, the wireless communication circuitry of sensor control device 102 can be configured to transmit data according to a plurality of connection parameters, including a connection interval maximum parameter, a slave latency parameter, and a supervision timeout parameter. In one embodiment, the connection interval maximum parameter can be set to a value equal to or less than 2 seconds, between 2 and 4 seconds, or equal to or greater than 4 seconds. The supervision timeout parameter can also be set to a value equal to or less than 6 seconds, or greater than 6 seconds. Similarly, handheld relay device 200 and reader devices 120 can communicate with each other over different advertising channels or different piconet physical channels, either concurrently or non-concurrently, so as to avoid data collision. While FIG. 4A depicts two reader devices 120, the embodiment can include any number of similar or dissimilar reader devices 120, including one device, three devices, four devices or more. Additionally, while FIG. 4A shows handheld relay device 200 as a centralized "hub" of the communication topology, a reader device 120, remote terminal 170 or other computer device capable of wireless communications can also be used in its place.

FIG. 4B depicts an alternative embodiment of a BTLE topology, with sensor control device 102, handheld relay device 200, and reader devices 120 configured as a BTLE scatternet 420, which comprises piconets 422, 424, and 426, wherein each piconet comprises a separate channel. In this embodiment, sensor control device 102 is configured as a slave device (S1) relative to handheld relay device 200, and handheld relay device 200 is configured as a master device (M1) relative to sensor control device. Reader devices 120 are each configured as slave devices (S2, S3) relative to handheld relay device 200, and handheld relay device is configured as a master device (M2, M3) relative to each reader device 120.

As with the prior embodiment, sensor control device 102 can communicate with handheld relay device 200 over an advertising channel or a piconet physical channel. Likewise, the wireless communication circuitry of sensor control device 102 can be configured to transmit data in accordance with the multiple connection parameters and options described with respect to topology 410 (FIG. 4A). Furthermore, in some embodiments, sensor control device 102 can be configured to operate in a discoverable state relative to the handheld relay device 200. The handheld relay device 200 can also be configured to operate in a discoverable state relative to one or more reader devices 120. In addition, one or more reader devices 120 may be configured to operate in a discoverable state relative to handheld relay device 200.

In still other embodiments of BTLE topologies (not shown), sensor control device 102 can be configured as a master device relative to handheld relay device 200, and handheld relay device can be configured as a slave device relative to sensor control device 102. Similarly, reader devices 120 can each be configured relative to handheld relay device 200 as described with respect to either FIG. 4A or 4B. That is, reader devices 120 can serve as either master or slave devices relative to handheld relay device 200, and vice versa.

Figure 5B:
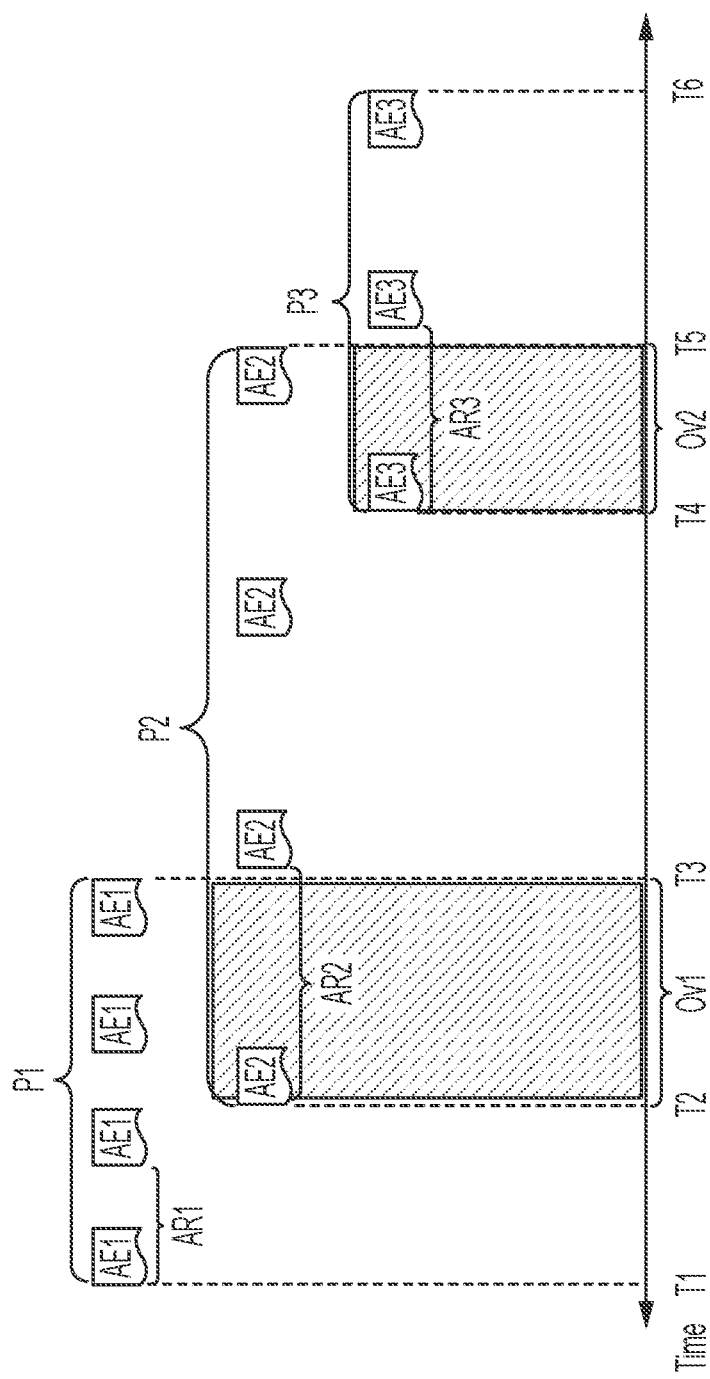
FIG. 5B is a timeline diagram depicting another example embodiment of an advertising scheme for use with an in vivo analyte monitoring system.

FIGS. 5A and 5B are timeline diagrams showing certain embodiments of Bluetooth and BTLE advertising schemes for use with in vivo analyte monitoring systems, as described above and depicted in FIGS. 1A, 1B, 4A and 4B. As described earlier, in recent years, the threat of unauthorized tracking of wireless devices has become a greater concern. For example, third parties may surreptitiously operate wireless device "trackers" at various geographical locations, which can then be used to track the movement of an individual based on a unique address of a wireless device carried by the individual. While certain wireless communication standard protocols have implemented countermeasures against such "trackers," these countermeasures may be inadequate. For example, in accordance with the Bluetooth and BTLE standard protocols, wireless devices can be configured to periodically generate random addresses or resolvable addresses, which can be used to obscure the true identity of a wireless device and prevent it from being tracked. However, "trackers" have become more sophisticated and can associate two or more randomly generated addresses with a particular wireless device. In particular, a "tracker" may observe a sequence of events in which a first device address disappears, followed by the appearance of a second device address. By analyzing the timing of such events, a "tracker" can deduce that the two device addresses actually correlate to a single wireless device that has replaced an old device address with a new device address.

FIG. 5A is a timeline diagram depicting an embodiment of a BTLE advertising scheme that can be used to resist efforts to track a sensor control device 102, handheld relay device 200, or reader device 200 of the previously described in vivo analyte monitoring systems. In one example, the wireless communication circuitry of sensor control device 102 begins transmitting a first set of advertisement packets (AE1) at time, T1, each having a first address. The advertisement packets are transmitted periodically at a first rate (AR1) for a first predetermined period of time (P1). The first address can be a randomly generated address. Similarly, the first rate (AR1) and the first predetermined period of time (P1) can be based at least in part on a randomly generated number.

Referring still to FIG. 5A, at time, T2, sensor control device 102 begins transmitting a second set of advertisement packets (AE2), wherein each packet has a second address. The second set of advertisement packets are transmitted periodically at a second rate (AR2) for a second predetermined period of time (P2). The second address (AE2) can be different from the first address (AE1), and can also be a randomly generated address. Similarly, the second rate (AR2) can be different from the first rate (AR1), and can also be based in part on a randomly generated number. The second predetermined period of time (P2) can be different from the first predetermined period of time (P1), and can also be based at least in part on a randomly generated number. At time, T3, the first predetermined period of time (P1) ends, and sensor control device 102 ceases to transmit the first set of advertisement packets (AE1). Sensor control device 102 continues to transmit the second set of advertisement packets (AE2) until time, T4, when the second predetermined period of time (P2) ends.

As shown by the shaded area of FIG. 5A, the advertising scheme includes an overlapping period of time (Ov1) in which the first and second predetermined periods of time (P1, P2) are overlapping. The duration of the overlapping period of time (Ov1) can be based at least in part on a randomly generated number. In this regard, a tracker would be unable to associate the first address and second address with sensor control device 102 based on the timing, initiation and cessation of the first and second advertisement packets.

FIG. 5B is a timeline diagram depicting another example embodiment of a BTLE advertising scheme that can be used to counteract efforts to track a sensor control device 102, handheld relay device 200, or reader device 120 of the previously described in vivo analyte monitoring systems. The embodiment shown in FIG. 5B is similar to that of FIG. 5A, except that a third set of advertisement packets (AE3) are additionally transmitted at time, T4, each having a third address. The third set of advertisement packets (AE3) is transmitted periodically at a third rate (AR3) for a third predetermined period of time (P3). The third address can be a randomly generated address. Similarly, the third rate (AR3) and third predetermined period of time (P3) can be based at least in part on a randomly generated number.

Referring still to FIG. 5B, at time, T5, the second predetermined period of time (P2) ends, and sensor control device 102 ceases to transmit the second set of advertisement packets (AE2). The third address can be different from the first and second addresses. The third rate (AR3) can be different from the first and second rates (AR1, AR2), and the third predetermined period of time (P3) can be also be different from the first and second predetermined periods of time (P1, P2). Sensor control device 102 continues to transmit the third set of advertisement packets (AE3) until time, T6, when the third predetermined period of time (P3) ends.

As shown by the shaded areas of FIG. 5B, the advertising schemes include two separate overlapping periods of time (Ov1, Ov2), wherein the first and second predetermined periods of time (P1, P2) are overlapping and the second and third predetermined periods of time (P2, P3) are overlapping. The duration of the second overlapping period of time (Ov2) can be based at least in part on a randomly generated number. As with the previous embodiment, a tracker would be unable to associate the first, second and third addresses with sensor control device 102 based on the timing, initiation and cessation of the first, second and third advertisement packets.

In the advertising scheme shown in FIG. 5B, the first and third predetermined periods of time (P1, P3) do not overlap with each other. It should be understood, however, that the advertising scheme can be configured such that the first and third predetermined periods of time (P1, P3) also overlap with each other, in addition to each overlapping with the second predetermined period of time (P2). Moreover, it should also be understood that the advertising schemes disclosed herein can also be configured such that any number of predetermined time periods (e.g., P1, P2, P3 and so on) can be either partially overlapping or completely overlapping.

In the embodiments described above, any or all of the first, second and third addresses can be 48-bit addresses, in accordance with the Bluetooth and BTLE standard protocols. Further, any or all of the first, second and third addresses can be generated by the one or more processors 166 of sensor control device 102 at the advent of a predetermined period of time. In an alternative embodiment, the addresses can be generated at other times such as, for example, during the manufacture of sensor control device 102, when sensor control device 102 is powered on (or power cycled), due to a change in geographical location of sensor control device 102, or at any other time prior to the advent of a predetermined period of time. In yet another embodiment, the addresses can be generated based on the expiration of a timer routine executed by sensor control device 102. Generated addresses can then be stored in memory 163, 165 of sensor control device 102 and later retrieved prior to the advent of a predetermined period of time.

In further embodiments of advertising schemes, any or all of the first, second and third addresses can be resolvable addresses. In accordance with the Bluetooth and BTLE standard protocol, for example, a resolvable address can have a first portion of an address which is randomly generated, and a second portion of the address which can be resolved using an identity resolution key (IRK). The identity resolution key can be a shared secret, which can be stored in and retrieved from the memory 163, 165 of sensor control device 102, the memory 280 of handheld relay device 200, the memory 323, 325 of one or more reader devices 120, or in a trusted computer system 180 accessible via a network 190.

Figure 5C:
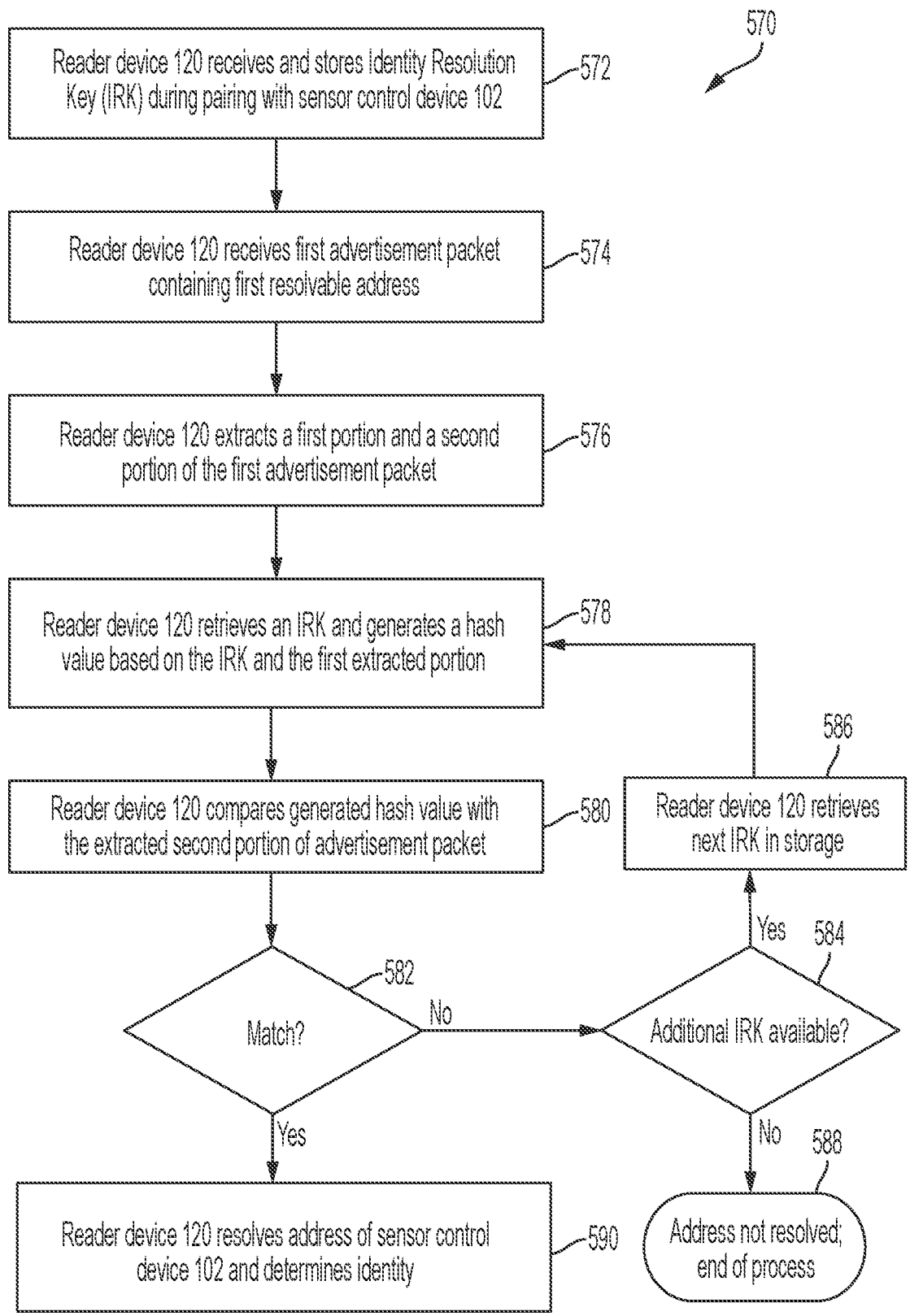
FIG. 5C is a flow diagram depicting an example embodiment of a method for resolving a resolvable address in an advertisement packet.

FIG. 5C is a flowchart diagram showing an example method in which reader device 120 attempts to determine identity of sensor control device 102 based on a first advertisement packet containing a resolvable address, as described in the above embodiments. Before describing the steps, it should be understood that one or more identity resolution keys (IRKs) can be generated by either sensor control device 102 or reader device 120, and exchanged during a pairing process. One or more IRKs can be stored in a memory 163, 165 of the sensor control device 102 and a memory 323, 325 of the reader device 120. In an alternative embodiment, one or more IRKs can be stored in a trusted computer system 180 for later retrieval by reader device 120, for example. It should also be understood that although the described method refers to reader device 120 as a device that can resolve the address of the sensor control device 102, the same method can be utilized by the handheld relay device 200 described in prior embodiments and depicted in FIGS. 1B and 2B.

Turning to FIG. 5C, at Step 572, a reader device 120 receives and stores the IRK during a pairing procedure with sensor control device 102. In another embodiment, for example, the reader device 120 can receive one or more IRKs from a trusted computer system 180 over a network 190, during a manufacturing process of reader device 120, or through any other means of communication. At Step 574, reader device 120 receives a first advertisement packet, similar to the ones described above and depicted in FIGS. 5A and 5B. The first advertisement packet includes a first address that is resolvable. At Step 576, reader device 120 extracts a first portion of the first advertisement packet. The extracted portion can comprise a 24-bit random part (prand). At Step 578, reader device 120 retrieves an IRK and generates a hash value based on the IRK. For example, a random address hash function, stored in a memory of the reader device 120, can be performed on the extracted portion (prand) of the first advertisement packet to generate a local hash value. At Step 580, reader device 120 compares the generated hash value (or local hash value) with a second extracted portion of the advertisement packet. For example, the second extracted portion of the advertisement packet can be a 24-bit hash value. At Step 582, if there is a match between the generated hash value (or local hash value) and the second extracted portion, then, at Step 590, reader device 120 is able to resolve the address of sensor control device 102 and determine its identity. If there is not a match, at Step 584, reader device 120 determines if there are any additional IRKs available for retrieval. If so, at Step 586, reader device 120 retrieves the next IRK and performs Steps 578, 580 and 582 in an attempt to resolve the address of sensor control device 102 using the next available IRK. If no remaining IRKs are available, the process ends at Step 588, and the reader device 120 is unable to resolve the address of sensor control device 102.

The steps in the flowchart of FIG. 5C can be used for any advertisement packet containing a resolvable address, including, for example, the second and third sets of advertisement packets described above and depicted in FIGS. 5A and 5B.

In all of the embodiments described herein, communication can occur between sensor control device 102 and reader device 120 and/or handheld relay device 200 using a Bluetooth or BTLE protocol. In every instance where communication between devices 102, 120 and 200 is to occur, a paired connection can be established between two devices as set forth in the Bluetooth and BTLE standard protocols. However, significant time gaps can exist between the sending of communications between devices 102 and 120 (or 200) and the maintenance of a paired connection, as well as the handshaking required for bringing up and tearing down paired connections, can require significant energy consumption by devices 102 and 120 (or 200). This is particularly problematic with sensor control device 102, which typically has a small battery with a low power budget.

Therefore, to conserve power, sensor control device 102 can be programmed to transmit data within the payload section of a typical advertisement packet (or channel) pursuant to the Bluetooth or BTLE standard protocols. Likewise, reader device 120 and/or handheld relay device 200 can be programmed to extract this data from the payload section of the advertisement packet.

The data within the advertising packet can be any data desired for transmission from sensor control device 102. One example is data indicative of the user sensed analyte level. This data can be encrypted to maintain confidentiality and for integration within any and all of the authentication schemes described herein. For example, communications sent from sensor control device 102, can be a BTLE advertising packet containing the encrypted analyte data 324 within the payload section of that advertising packet.

Figure 6A:
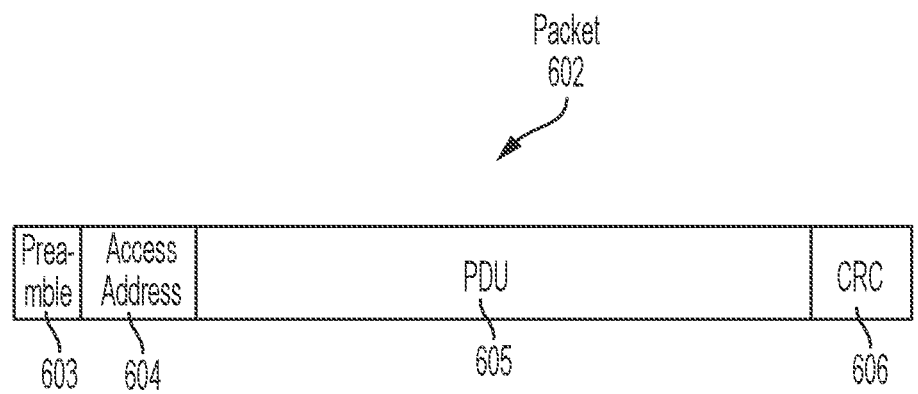
FIGS. 6A-B are block diagrams depicting example embodiments of advertisement packets comprising analyte data.

FIG. 6A is a block diagram depicting an example embodiment of a BTLE advertising packet 602, having a preamble 603, an access address 604 (which together form a header section), a protocol data unit (PDU) 605, and a cyclic redundancy check (CRC) 606. In this embodiment, advertising packet 602 is a connectable undirected advertising packet type, however, packet 602 can be other types as well including a connectable directed advertising packet type, a non-connectable undirected advertising packet type, or a scannable undirected advertising packet type.

Figure 6B:
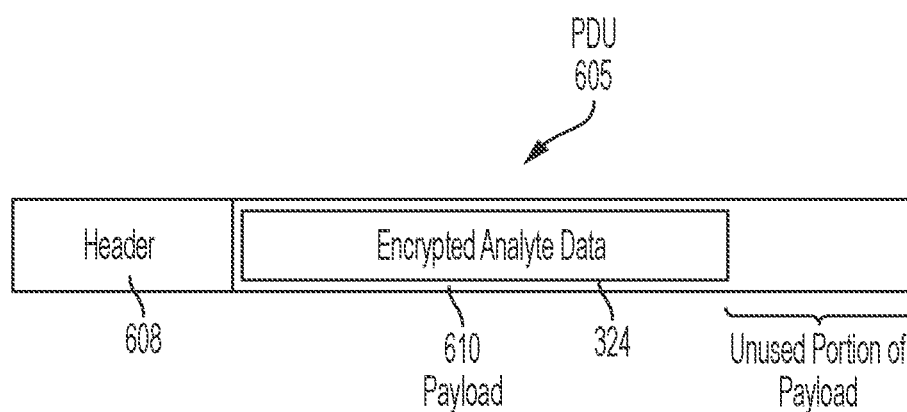

Within PDU 605 is an advertising header section 608 and an advertising payload section 610, as shown in FIG. 6B. The encrypted analyte data 324 is stored within advertising payload section 610. The encrypted data should be smaller than the maximum payload of the advertising packet, although analyte data that is too large can be split across subsequent advertising packets if desired. Various amounts of data can be included in the advertising packet. In one embodiment, the BTLE protocol allows 22 bytes of payload to be included in an advertising packet, and thus the encrypted data is 22 bytes or less in size. (FIG. 6B shows some of the total available payload as unused.) Encryption schemes such as AES128 use a 16 byte block size, which can be accommodated within the advertising payload. Depending on the size of the measurement data for a single sensing of analyte level, at least one analyte level measurement can fit within the 16 byte encrypted block. In some embodiments, the data for two or three (or more) analyte level measurements will fit within the 16 byte encrypted block. In those embodiments, sensor control device 102 can be programmed to insert the two or three (or more) most recent analyte level measurements into each 16 byte encrypted block. Reader device 120 or handheld relay device 200 can then reconstruct the recent analyte level trends for the user, i.e., both current and limited historical analyte data, in case one or more prior measurements were not successfully transmitted by sensor control device 102 or received by reader device 120 or handheld relay device 200.

The period between subsequent advertising transmissions from sensor control device 102 can be set as desired. For example, the interval between the transmission of advertising packets can be one minute, two minutes, five minutes, 10 minutes, 15 minutes, one hour, and so forth. Furthermore, this interval can be variable so as to accommodate the user's preferences or conserve battery life, etc.

In embodiments that utilize this advertising packet approach, sensor control device 102 and reader device 120 (or handheld relay device 200) can first establish a typical paired connection pursuant to the Bluetooth or BTLE standard protocols. This will allow the devices to become bonded so that each will recognize the other and will only conduct communications with the other. While this paired connection is established, devices 102 and 120 (or 200) can exchange information so as to create any of the authentication regimes described herein. For example, device 102 can transmit an identifier. In some embodiments, communication between multiple sensor control devices and one reader device (or one handheld relay device), or communication between multiple reader devices (or handheld relay devices) and one sensor control device is permitted. This is described in greater detail within U.S. Patent Application Ser. No. 62/001,343, filed May 21, 2014, which is incorporated by reference herein in its entirety for all purposes.

When using the advertising packets, sensor control device 102 will be communicating in a unidirectional manner, with analyte data transmitted on a scheduled basis without prompting by reader device 120. Should reader device 120 need to transmit to sensor control device 102, then a paired connection can be created.

Also provided herein are example embodiments of devices (and methods of operating the same) having a test strip interface that can be activated upon insertion of a test strip. These devices can include handheld relay device 200, reader device 120, and/or an in vitro analyte meter. These devices can be kept in a power-off state, or a relatively low power (e.g., sleep) state, to minimize current draw from the power supply and maximize operating life. Upon insertion of a test strip, the device hardware and/or software can cause the device to exit the power-off (or low-power) state and enter a power-on (or relatively higher power) state for regular operation.

Figure 7A:
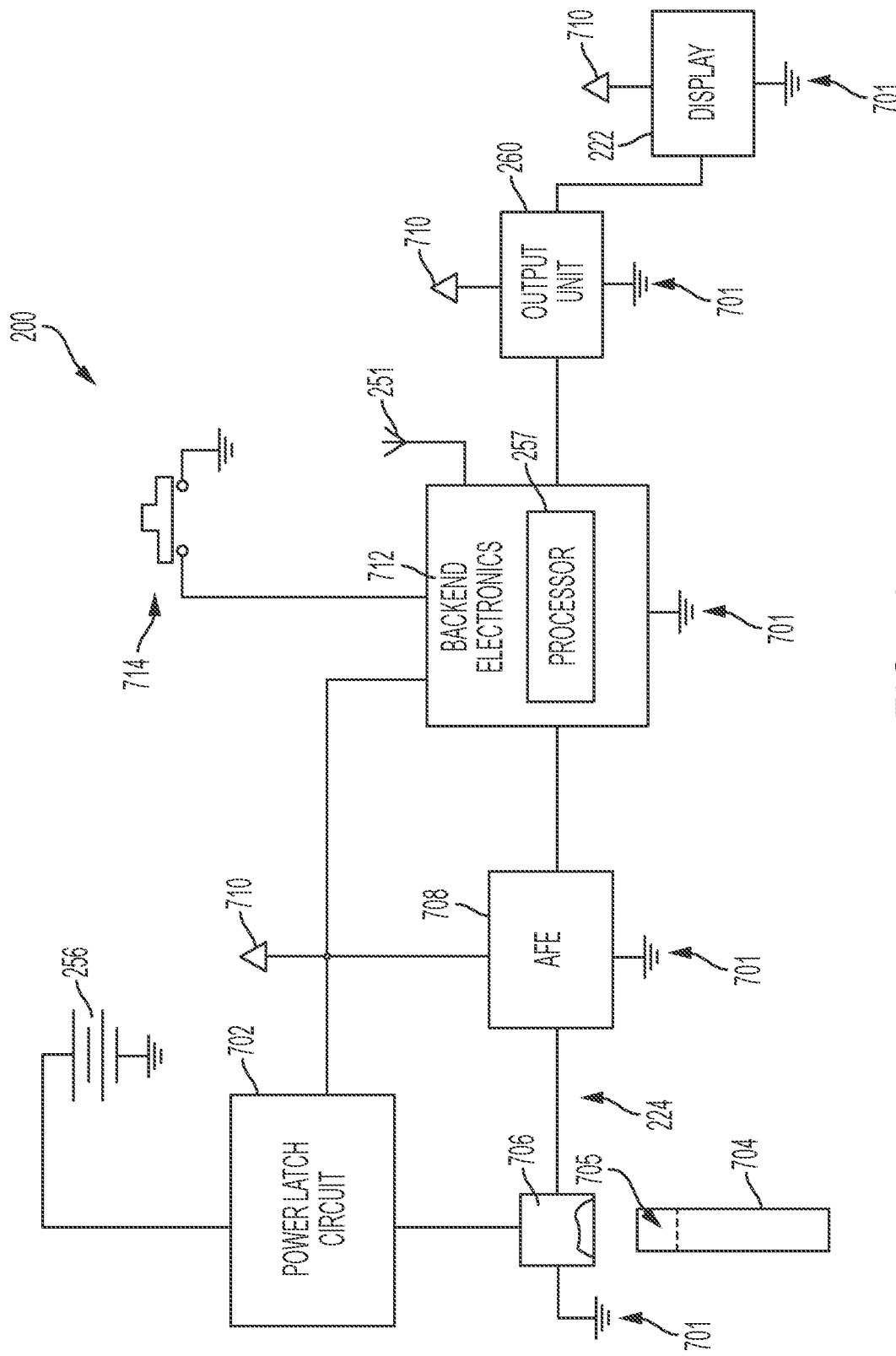
FIG. 7A is a block diagram depicting an example embodiment of a handheld reader device with power latch circuitry.

FIG. 7A is a block diagram depicting an example embodiment of handheld relay device 200 with power latch (or connection) circuitry 702. Here, power latch circuitry 702 is electrically coupled with test strip port 706, power supply 256, and power distribution node 710 (e.g., a power plane). Test strip port 706 is also coupled to a reference node 701 (e.g., ground) and is configured to output an analog signal indicative of an analyte level in a sample on test strip 704 to analog front end (AFE) circuitry 708, which can include conditioning circuitry (e.g., an operational amplifier) that conditions the analog signal for conversion to digital form by an A/D converter (not shown) that can be, for example, in AFE 708 or in back end electronic circuitry 712. Test strip port 706 and AFE 708 can form test strip interface 224. Back end electronic circuitry 712, can include one or more processors 257 as well as one or more other components shown in FIG. 2B (e.g., memory 280, RF transceiver 252, multi-functional circuitry 252, etc.). Back end circuitry 712 can be coupled with RF antenna 251, an optional secondary switch 714, and output unit 260, which is in turn coupled with display 222.

Power latch circuitry 702 can be configured to sense or detect the insertion of test strip 704 into test strip port 706 and, in response, connect power supply 256 to an electrical load, which can include all or part of the remaining circuitry within relay device 200. Power latch circuitry 702 can also be configured to maintain the connection of power supply 256 after test strip 704 is removed, and to continue to maintain the connection until instructed to disconnect, such as by processor 257. In this manner, relay device 200 can be kept in the power-off (or a relatively low power) state until needed by the user to perform an analyte measurement with test strip 704. Although described with respect to handheld relay device 200, these methods and circuits can likewise be implemented in embodiments of other devices having a test strip interface such as reader device 120 or an in vitro meter.

In FIG. 7A, test strip 704 can include a conductive region 705 on a first end that is inserted into test strip port 706. The conductive region 705 can include, for example, one or more conductive traces or bars that electrically connect contacts in test strip port 706 and create a closed circuit (e.g., a short) to reference node 701 (see also FIG. 7B). Power latch circuit 702 can sense or detect this connection to reference node 701 and subsequently connect power supply 256 (e.g., a rechargeable battery, a coin cell battery, or otherwise) to the device's power node 710. This power connection supplies power to each of the other circuits within device 200 that are coupled to power node 710 and allows these circuits to initiate operation or exit low-power sleep states and transition to a relatively higher power state, such as a power-on state.

Figure 7B:
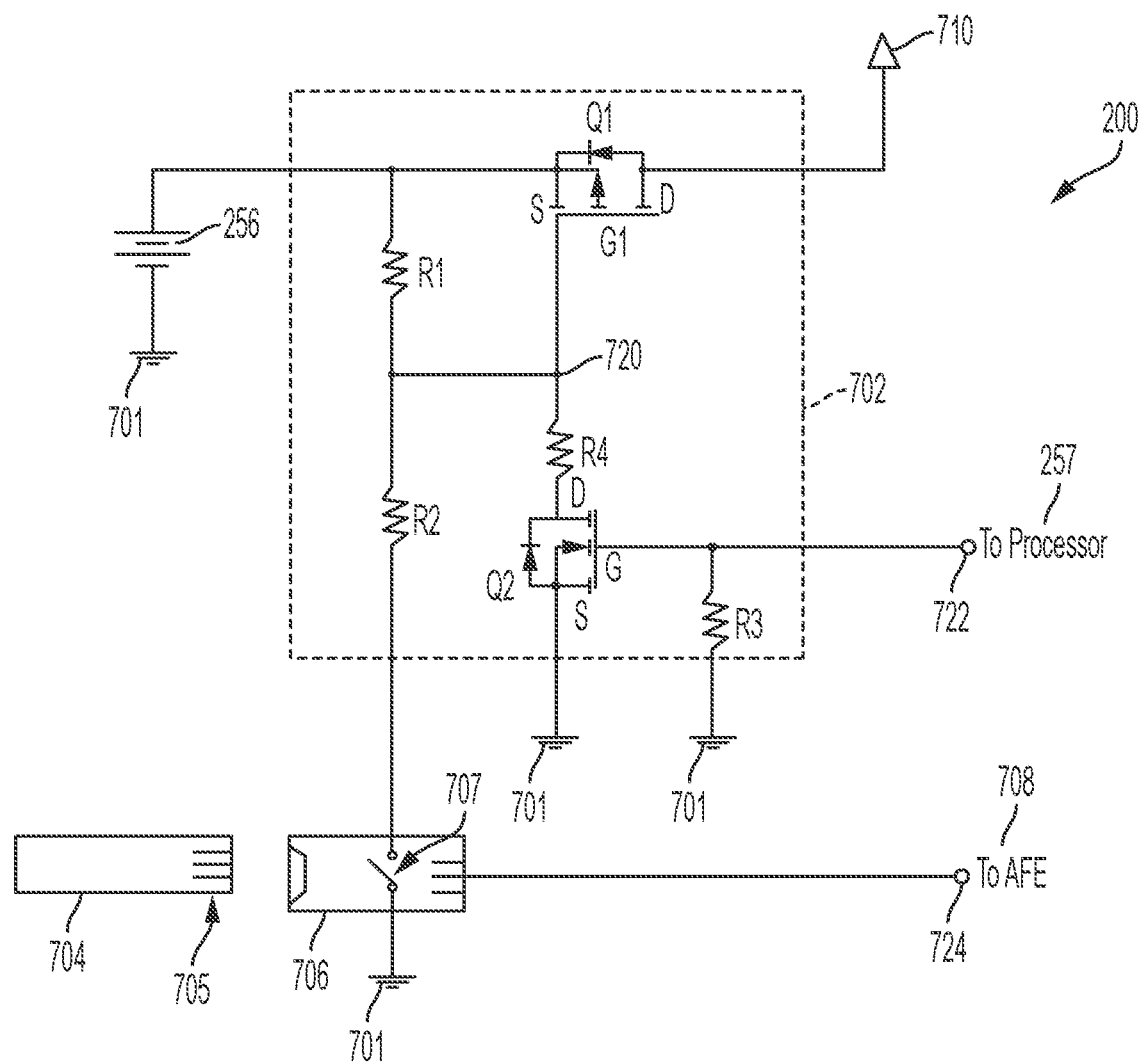
FIG. 7B is a schematic diagram depicting an example embodiment of power latch circuitry.

FIG. 7B is a schematic diagram depicting an example embodiment of power latch circuitry 702 and its connections in greater detail. Here, power latch circuitry 702 includes a first transistor Q1 coupled with a second transistor Q2. In this embodiment, Q1 is a p-channel enhanced MOSFET and Q2 is an n-channel enhanced MOSFET, although other types of field effect transistors (FETs) can be used as well, with modifications as will be apparent to those of ordinary skill in the art. Those other transistor types can include, but are not limited to, JFET, MOSFET without bulk, MOSFET depleted, MESFET, or IGFET. Processes with low gate leakages and low drain-source leakages are particularly suitable for use with the control circuit embodiments described herein.

The drain of Q1 is connected to power node 710 and the source of Q1 is connected to power source 256 and a first end of resistor R1. The second end of R1 is connected to the gate of Q1, the drain of Q2, and a first end of resistor R2 (represented by node 720). The source of Q2 is connected to reference node 701 and the gate of Q2 is connected to a first end of resistor R3 and node 722, which can receive a signal from processor 257. Resistor R3 is coupled between the gate of Q2 and reference node 701.

Test strip port 706 communicates with AFE 708 through node 724. The potential connection of conductive region 705 with corresponding contacts within test strip port 706 is visualized here as a switch 707. (In other embodiments, the insertion of strip 704 can trigger an actual switch to signal insertion.) In this embodiment, insertion of strip 704 effectively closes switch 707, and connects one end of R2 to reference (ground) node 701 and pulls node 720 low, which biases the gate of Q1 towards a low voltage (e.g., a digital "0"). This activates Q1 (e.g., allows current to flow across the drain and source) and connects power supply 256 to power distribution node 710. Each circuit connected to power node 710 can then draw current from supply 256, including back end electronics 712 and processor 257. Processor 257 can then enter its power-on (or relatively high power) state, perform an initialization routine if necessary, and generate a latch signal at node 722.

The latch signal at node 722 is a high voltage signal in this embodiment (e.g., a digital "1") and activates Q2, which in turn further biases node 720 towards a low voltage. At this point, circuit 702 can be maintained in its power-supply connected state, such that removal of strip 704 (and opening of switch 707) will not disconnect power supply 256 from power node 710. Although not shown, a user accessible switch can also be coupled between node 720 and ground, such that the user can cause connection of supply 256 and activate device 200 without the insertion of strip 704.

In many embodiments R1 is chosen to have a value greater than R2. A high value for R1 minimizes leakage current through Q2. R3 assists in pulling node 722 towards the low voltage of reference node 701 when processor 257 is disconnected, to prevent inadvertent activation of Q2. The embodiment of FIG. 7B is described as functioning with signals of various voltage polarities (e.g., high and low), but those polarities are used only as an example and the same or similar functionality can be achieved by implementing circuit 702 to operate with polarity levels opposite to those described here.

After being activated, handheld relay device 200 can perform various tasks. Wireless communication circuitry of relay device 200 can transmit an attempt to establish a communication link with another device (e.g., sensor control device 102 or reader device 120), for example, by initiating the transmission of an advertising signal according to a Bluetooth or BTLE protocol, and negotiate establishment of the wireless link. This can occur directly as a result of connection of the power supply to the wireless communication circuitry (through node 710), or indirectly as a result of processing circuitry 257 instructing or otherwise causing the wireless communication circuitry to transmit the attempt.

Relay device 200 can also begin the steps to conduct a sample measurement, such as by notifying (audibly, visually, through vibration, etc.) the user to dose strip 704, monitoring for strip fill, notifying the user when enough blood has been applied, performing the analyte measurement, displaying the result, and communicating the results to another device (e.g., to sensor control device 102 for calibration or to reader device 120). In some embodiments, relay device 200 does not include a graphical display, or lacks a display altogether, and upon establishing the connection, reader device 120 is used as the user interface to communicate with the user and control (or assist in controlling) the execution of the various sample measurement steps, and then display the measurement results.

Processor 257 maintains control over latch circuit 702 via the latching signal applied to node 722. Processor 257, executing instructions from memory, can disconnect power supply 256 by changing the polarity of the latching signal at node 722 from high to low. For example, processor 257 can have a "time-out" function and can monitor the amount of time that, for example, has passed since insertion of strip 704, since completion of the measurement, since display of the results, or since the last user action was taken, and upon reaching a maximum time duration of time, then change the polarity of the latching signal to disconnect supply 256.

Referring back to FIG. 7A, optional switch 714 is coupled with back end electronics 712 and can be used to reset device 200. For example, if the communication link (e.g., BTLE) between relay device 200 and another device is lost, then the user can use switch 714 to reset back end electronics 712 (or a sub-component thereof, such as processor 257 or the communication circuitry) to reestablish the communication link.

The embodiments described with respect to FIGS. 7A and 7B can offer a number of improvements over conventional devices. For example, one such improvement is the increase in operating life achieved by enabling device activation upon insertion of a test strip, and by enabling device deactivation upon removal of the test strip or subsequently thereafter under the control of processing circuitry or a timer. The increase in operating life can be achieved by minimizing the draw of current from the power supply to only those times when the device is in use, and by keeping all or a majority of the device circuitry in the power-off (or low power) state during those times when the device is not being used.

In many instances, entities are described herein as being coupled to other entities. The terms "coupled" and "connected" (or any of their forms) are used interchangeably herein and, in both cases, are generic to the direct coupling of two entities (without any non-negligible (e.g., parasitic) intervening entities) and the indirect coupling of two entities (with one or more non-negligible intervening entities). Where entities are shown as being directly coupled together, or described as coupled together without description of any intervening entity, those entities can be indirectly coupled together as well unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A method for advertising a sensor control device in an in vivo analyte monitoring system, the method comprising:
generating a first address associated with the sensor control device;
transmitting periodically, at a first advertising rate for a first predetermined period, one or more first advertisement packets comprising the first address;
generating a second address associated with the sensor control device, wherein the first address is different from the second address; and
transmitting periodically, at a second advertising rate for a second predetermined period, one or more second advertisement packets comprising the second address, wherein the first predetermined period overlaps with the second predetermined period; and
wherein the transmitting steps comprise wirelessly transmitting the advertisement packets using one of a near field communication (NFC) protocol, a RFID protocol, a Bluetooth or Bluetooth Low Energy protocol, a Wi-Fi protocol, or a proprietary protocol.

2. The method of claim 1, wherein the first advertising rate is different from the second advertising rate.

3. The method of claim 1, wherein either or both of the first advertising rate and the second advertising rate is based at least in part on a randomly generated number.

4. The method of claim 1, wherein the duration of the overlap between the first predetermined period and the second predetermined period is based at least in part on a randomly generated number.

5. The method of claim 1, wherein either or both of the first address and the second address is a randomly generated address.

6. The method of claim 1, wherein at least one of the first address or the second address is a resolvable address, wherein the resolvable address is adapted to be resolved to an address associated with the sensor control device using an identity resolution key, and wherein the resolvable address comprises:
a first portion of which is based on a randomly generated number; and
a second portion of which is based on the identity resolution key.

7. The method of claim 6, further comprising:
receiving, by a reader device, at least one of the first advertisement packets or the second advertisement packets, wherein the at least one of the first advertisement packets or the second advertisement packets comprises the resolvable address;
retrieving, by the reader device, the identity resolution key; and
resolving, by the reader device, the identity of the sensor control device (102) using the at least one of the first advertisement packets or the second advertisement packets and the identity resolution key.

8. The method of claim 6, further comprising:
receiving, by a reader device, at least one of the first advertisement packets or the second advertisement packets, wherein the at least one of the first advertisement packets or the second advertisement packets comprises the resolvable address;
extracting the first portion and the second portion from the at least one of the first advertisement packets or the second advertisement packets;
performing, by the reader device, an iterative comparison loop, the steps of the iterative comparison loop comprising:
retrieving, by the reader device, the identity resolution key;
generating a hash value based on the retrieved identity resolution key and the first extracted portion;
comparing the generated hash value to the second extracted portion;
determining, if there is a match between the generated hash value and the second extracted portion, an identity of the sensor control device; and
identifying, if there is not a match between the generated hash value and the second extracted portion, a next identity resolution key to retrieve.

9. An in vivo analyte monitoring system comprising a sensor control device, the sensor control device comprising:
- wireless communication circuitry adapted to wirelessly transmit data;
- one or more processors;
- memory on which one or more instructions are stored that, when executed by the one or more processors, cause the one or more processors to:
  - generate a first address associated with the sensor control device;
  - transmit periodically, at a first advertising rate for a first predetermined period, one or more first advertisement packets comprising the first address;
  - generate a second address associated with the sensor control device, wherein the first address is different from the second address; and
  - transmit periodically, at a second advertising rate for a second predetermined period, one or more second advertisement packets comprising the second address; and
- wherein the first predetermined period overlaps with the second predetermined period; and
- wherein the transmitting steps comprise wirelessly transmitting the advertisement packets using one of a near field communication (NFC) protocol, a RFID protocol, a Bluetooth or Bluetooth Low Energy protocol, a Wi-Fi protocol, or a proprietary protocol.

10. The system of claim 9, wherein the first advertising rate is different from the second advertising rate.

11. The system of claim 9, wherein either or both of the first advertising rate and the second advertising rate is based at least in part on a randomly generated number.

12. The system of claim 9, wherein a duration of the overlap between the first predetermined period and the second predetermined period is based at least in part on a randomly generated number.

13. The system of claim 9, wherein either or both of the first address and the second address is a randomly generated address.

14. The system of claim 9, wherein at least one of the first address or the second address is a resolvable address, wherein the resolvable address is resolved to an address associated with the sensor control device using an identity resolution key, and wherein the resolvable address comprises:
- a first portion of which is based on a randomly generated number; and
- a second portion of which is based on the identity resolution key.

15. The system of claim 14, further comprising a reader device, the reader device comprising:
- wireless communication circuitry;
- one or more processors;
- memory on which one or more instructions are stored that, when executed by the one or more processors, cause the one or more processors to:
  - receive at least one of the first advertisement packets or the second advertisement packets, wherein the at least one of the first advertisement packets or the second advertisement packets comprises the resolvable address;
  - retrieve the identity resolution key; and
  - resolve an identity of the sensor control device using the at least one of the first advertisement packets or the second advertisement packets and the identity resolution key.

* * * * *